(12) United States Patent
Belardo et al.

(10) Patent No.: US 12,350,189 B2
(45) Date of Patent: Jul. 8, 2025

(54) MENSTRUAL COLLECTION DEVICE, APPLICATOR AND A METHOD OF INSERTING A MENSTRUAL COLLECTION DEVICE WITH AN APPLICATOR

(71) Applicant: Menstrual Mates, Inc., Lewes, DE (US)

(72) Inventors: Cynthia Belardo, West Lafayette, IN (US); Drew Jarvis, Bloomington, IN (US); Benjamin Ettinger, Evergreen, CO (US); Sean Kleinschmidt, Carmel, IN (US); Grant Chapman, Indianapolis, IN (US)

(73) Assignee: Menstrual Mates, Inc., Lewes, DE (US)

( * ) Notice: Subject to any disclaimer, the term of this patent is extended or adjusted under 35 U.S.C. 154(b) by 0 days.

(21) Appl. No.: 17/664,726

(22) Filed: May 24, 2022

(65) Prior Publication Data

US 2023/0019578 A1    Jan. 19, 2023

Related U.S. Application Data

(60) Provisional application No. 63/223,155, filed on Jul. 19, 2021.

(51) Int. Cl.
*A61F 5/455* (2006.01)
*A61F 5/44* (2006.01)

(52) U.S. Cl.
CPC .......... *A61F 5/4553* (2013.01); *A61F 5/4404* (2013.01)

(58) Field of Classification Search
CPC .............................. A61F 5/4404; A61F 5/4553
See application file for complete search history.

(56) References Cited

U.S. PATENT DOCUMENTS 3,845,766 A    11/1974    Zoller
4,010,751 A    3/1977    Ring
(Continued)

FOREIGN PATENT DOCUMENTS

BR    D17100477-0001    5/2012
BR    302015005328-0001    12/2016
(Continued)

OTHER PUBLICATIONS

Onpery, Menstrual Cup, https://www.onpery.com/pages/product-menstrual-cup, last visited Feb. 2, 2022.
(Continued)

*Primary Examiner* — Rebecca E Eisenberg
*Assistant Examiner* — Rachel O'Connell
(74) *Attorney, Agent, or Firm* — DINSMORE & SHOHL LLP

(57) ABSTRACT

A menstrual collection device, an applicator and a method of inserting a menstrual collection device within a vaginal canal. The menstrual collection device includes ribs and thin-walled panels or membranes that are recessed from, extend between and are formed integral to the ribs. The ribs and thin-walled panels or membrane allow for the menstrual collection device to hold its shape and collect fluid while still being able to be folded to reduce the surface area of the collection device and fit within the applicator. The applicator tip is flexible such that it allows for menstrual collection device to pass therethrough while still applying a force by to the menstrual collection device to aid in the opening of the collection device to a fully open state.

5 Claims, 29 Drawing Sheets

(56) References Cited

U.S. PATENT DOCUMENTS

| | | | |
|---|---|---|---|
| 6,450,985 B1 * | 9/2002 | Schoelling | A61F 13/26 604/15 |
| 6,796,973 B1 | 9/2004 | Contente et al. | |
| D602,587 S | 10/2009 | Edgett et al. | |
| 8,029,456 B2 | 10/2011 | Fung | |
| D675,733 S | 2/2013 | Karapasha et al. | |
| D746,452 S | 12/2015 | Petrova | |
| D760,897 S | 7/2016 | Teo | |
| 9,427,361 B2 | 8/2016 | Buell et al. | |
| D772,409 S | 11/2016 | Buell et al. | |
| D787,673 S | 5/2017 | Buell et al. | |
| 9,827,136 B2 | 11/2017 | Shaviv | |
| D816,839 S | 5/2018 | Buell et al. | |
| D819,206 S | 5/2018 | Buell | |
| D819,813 S | 6/2018 | Buell et al. | |
| D819,814 S | 6/2018 | Buell | |
| D829,905 S | 10/2018 | Buell et al. | |
| D836,196 S | 12/2018 | Ahn | |
| D837,980 S | 1/2019 | Sedic | |
| D841,161 S | 2/2019 | Buell et al. | |
| D841,808 S | 2/2019 | Drach | |
| D842,466 S | 3/2019 | Buell et al. | |
| D842,467 S | 3/2019 | Buell | |
| D842,993 S | 3/2019 | Buell et al. | |
| 10,357,395 B2 | 7/2019 | Miller et al. | |
| 10,441,401 B2 | 10/2019 | Kanner et al. | |
| D872,262 S | 1/2020 | Buell | |
| D892,324 S | 8/2020 | Yi et al. | |
| D894,386 S | 8/2020 | LeClerc | |
| D895,798 S | 9/2020 | Newman et al. | |
| D895,799 S | 9/2020 | Newman et al. | |
| D901,684 S | 11/2020 | Angert | |
| D910,174 S | 2/2021 | Mills et al. | |
| D930,829 S | 9/2021 | Stoebe-Latham | |
| 11,154,416 B2 | 10/2021 | Miller et al. | |
| 11,234,857 B2 | 2/2022 | Miller et al. | |
| D965,780 S | 10/2022 | Kagiwada et al. | |
| D977,637 S | 2/2023 | Brush et al. | |
| 11,583,433 B2 | 2/2023 | Brush et al. | |
| 2005/0277867 A1 * | 12/2005 | Minoguchi | A61F 13/26 604/15 |
| 2012/0041354 A1 | 2/2012 | Dougherty, Jr. | |
| 2014/0012216 A1 * | 1/2014 | Shaviv | A61F 5/4553 29/428 |
| 2018/0021120 A1 | 1/2018 | Kanner et al. | |
| 2018/0125726 A1 | 5/2018 | Buell et al. | |
| 2019/0000680 A1 * | 1/2019 | DeOliveira | A61F 13/2071 |
| 2019/0151136 A1 | 5/2019 | Garriga I Rodo | |
| 2019/0282350 A1 * | 9/2019 | Conti | A61F 6/12 |
| 2020/0060865 A1 | 2/2020 | Hwang | |
| 2020/0155363 A1 | 5/2020 | Dougherty et al. | |
| 2020/0375788 A1 | 12/2020 | Zhang | |
| 2021/0100693 A1 | 4/2021 | Buell et al. | |
| 2021/0113363 A1 | 4/2021 | Evans et al. | |
| 2021/0137725 A1 | 5/2021 | Shaviv et al. | |
| 2021/0290448 A1 | 9/2021 | Khan et al. | |
| 2022/0047411 A1 | 2/2022 | Miller et al. | |
| 2022/0296409 A1 | 9/2022 | Miller et al. | |
| 2022/0378627 A1 | 12/2022 | Agbo et al. | |
| 2023/0099175 A1 | 3/2023 | Adame et al. | |

FOREIGN PATENT DOCUMENTS

| | | | |
|---|---|---|---|
| CN | 203634351 | | 6/2014 |
| CN | 303076209 | | 1/2015 |
| CN | 204971787 U | | 1/2016 |
| CN | 109172950 | | 1/2019 |
| CN | 109172950 A * | | 1/2019 ......... A61M 1/0009 |
| CN | 305067360 | | 3/2019 |
| CN | 305562188 | | 1/2020 |
| CN | 305967783 | | 8/2020 |
| CN | 306177252 | | 11/2020 |
| CN | 212308172 | | 1/2021 |
| CN | 306425393 | | 3/2021 |
| DE | 402020000186-0001 | | 11/2020 |
| DE | 202021000536 U1 | | 3/2021 |
| DE | 402021100711-0001 | | 12/2021 |
| EM | 000526041 | | 6/2006 |
| EM | 002103705 | | 9/2012 |
| EM | 00234584 | | 12/2013 |
| EM | 002515130 | | 8/2014 |
| EM | 002854471 | | 10/2015 |
| EM | 002912212 | | 12/2015 |
| EM | 003313105 | | 11/2016 |
| EM | 003496983 | | 12/2016 |
| EM | 003179886 | | 2/2017 |
| EM | 003934124 | | 5/2017 |
| EM | 004561165 | | 1/2018 |
| EM | 004711075 | | 2/2018 |
| EM | 005226651 | | 6/2018 |
| EM | 005285202 | | 7/2018 |
| EM | 005808813 | | 11/2018 |
| EM | 005842747 | | 12/2018 |
| EM | 007194014 | | 2/2020 |
| EM | 008110076 | | 12/2020 |
| EM | 008409551 | | 2/2021 |
| EM | 008821854 | | 1/2022 |
| EP | 1796608 | | 6/2007 |
| EP | 2407136 | | 1/2012 |
| EP | 3485854 | | 5/2019 |
| EP | 3 613 390 | | 2/2020 |
| ES | D0525179-04 | | 4/2017 |
| FR | 20162226-002 | | 8/2016 |
| GB | 9007194014-0001 | | 11/2019 |
| GB | 9008110076-0001 | | 8/2020 |
| GB | 6114702 | | 1/2021 |
| IN | 201721016822 | | 11/2018 |
| IN | 338955-001-0001 | | 12/2021 |
| JP | 3998462 | | 10/2007 |
| JP | 2018089376 | | 6/2018 |
| KR | 101834197 | | 3/2018 |
| KR | 20190130525 | | 11/2019 |
| KR | 102331755 | | 11/2021 |
| MX | 51954-0001 | | 1/2018 |
| NO | 086404-0001-0001 | | 9/2019 |
| TW | M616724 | | 9/2021 |
| WO | D103644-001 | | 4/2019 |
| WO | 2019198876 | | 10/2019 |
| WO | 2019211802 A1 | | 11/2019 |
| WO | 2021106012 | | 6/2021 |
| WO | WO-2021106012 A1 * | 6/2021 | ............ A61F 5/451 |
| WO | 2022208081 A1 | | 10/2022 |
| WO | 2023034401 A1 | | 3/2023 |

OTHER PUBLICATIONS

Sirona, Menstrual Cups, https://www.thesirona.com/buy/period-care/menstrual-cups, last visited Feb. 2, 2022.

Enna Menstrual Cup, Ecareyou Innovation, S.L., https://ennawomen.com/menstrual-cup/, last visited Jun. 21, 2022.

Revive Bladder Support, Rinovum Subsidiary 2, LLC, (d/b/a/ Revive), https://userevive.com/, last visited Jun. 21, 2022.

Intimina Lily Cup, Lelo, Inc. (d/b/a Intimina), https://www.intimina.com/lily-cup, last visited Jun. 28, 2022.

International Search Report and Written Opinion, United States Patent and Trademark Office, Application No. PCT/US22/73688, Oct. 4, 2022.

Products of Design, https://productsofdesign.sva.edu/blog/ora-menstrual-cup-and-applicator, last visited May 10, 2023.

Fillow, Inc. https://fillowme.com/, last visited May 10, 2023.

Kickstarter Fillow, https://www.kickstarter.com/projects/fillow/fillow-the-no-risk-period-disc, last visited May 10, 2023.

Emm Technology Ltd., https://www.emm.co/, last visited May 10, 2023.

The Verge, https://www.theverge.com/2023/2/3/23578371/emm-femtech-menstrual-cup-wearables, last visited May 10, 2023.

Lyv Life, Inc., https://cora.life/collections/reusable/products/cora-menstrual-cup, last visited May 10, 2023.

Gals Bio Ltd., https://www.tulipon.com/, last visited May 10, 2023.

Dame Products, Reusable Applicator, http://wearedame.co/products/reusable-applicator,Feb. 3, 2022.

(56) References Cited

OTHER PUBLICATIONS

Spicytec, reusable tampon applicator, http://www.spicytec.com/2018/03/d-worlds-first-reusable-tampon.html, Feb. 3, 2022.
Ecareyou Innovation, S.L., Menstrual cup, https://ennawomen.com/menstrual-cup/, Jun. 21, 2022.
Ovala, Inc., Bladder support, https://userevive.com/, Jun. 21, 2022.
Invitation to pay additional Fees and, Where Applicable, Protest Fee and Communication Relating to the Results of the Partial International Search Report dated Jan. 30, 2025 pertaining to International application No. PCT/US2024/051053 filed Oct. 11, 2024, pp. 1-16.
European Patent Office Communication pursuant to Rule 164(1) EPC issued in EP 22846751.0 dated Apr. 24, 2025.

* cited by examiner

MENSTRUAL COLLECTION DEVICE, APPLICATOR AND A METHOD OF INSERTING A MENSTRUAL COLLECTION DEVICE WITH AN APPLICATOR

CROSS-REFERENCE TO RELATED APPLICATION

This patent application claims benefit to U.S. Provisional Patent Application No. 63/223,155 filed Jul. 19, 2021, which is hereby incorporated by reference in its entirety as part of the present disclosure.

FIELD OF THE INVENTION

The present disclosure relates to menstrual products, and more specifically to a menstrual collection device, an applicator and a method of inserting the menstrual collection device with an applicator with the menstrual collection device configured to be insertable within the applicator and deployed through an opening in the tip of the applicator.

BACKGROUND OF THE INVENTION

A menstrual collection device is a reusable period product that menstruators use during menstruation. The purpose of the device is to collect period fluid during menstruation as an alternative to tampons and pads, which absorb period fluids rather than collect them. Using a menstrual collection device as an alternative to tampons and pads can also save money and reduce the impact on the environment. A menstrual collection device is commonly made of flexible materials to allow it to bend and in turn make it easier and more comfortable to insert the device into the vaginal canal during menstruation. The device can include many different colors and be many different shapes and sizes. The most common shapes, without limitation, are hemispherical with or without a rim, V-shaped with or without rim, rounded with rim, and slanted with a rim. However, existing menstrual collection devices can be uncomfortable and/or challenging to insert manually into the vaginal canal and, if a device is used to aid in the insertion of a menstrual collection device, the combination of the collection device and applicator can cause the collection device to regularly not be inserted properly and/or fully opened. Additionally, some menstrual collection devices have thin sidewalls that are easily deformable and do not maintain structural rigidity required to maintain a fully open state within the vaginal canal whether inserted with the assistance of an applicator or manually. By not opening fully, the collection device does not capture substantially all menstrual fluid.

SUMMARY OF THE INVENTION

The present disclosure is generally directed to a menstrual collection device, an applicator and a method of inserting a menstrual collection device within a vaginal canal with the applicator.

In an embodiment, the menstrual collection device includes a housing that is open at a first end and tapers to a base at a second closed end from which a stem extends. The housing defines a cavity therein and includes a frame that has a first thickness, panels or membrane that have a second thickness and extend between the frame and a rim that extends from the frame to delimit the first end of the housing.

The frame can include a plurality of ribs or thick-walled sections including a first rib, a second rib, a third rib and a fourth rib. The first rib can extend vertically about the housing. The second rib can be spaced from the first rib and extend vertically about the housing. The third rib can extend from a first end of the first and second rib continuously about an upper end of the housing. The fourth rib can extend from a second end of the first and second rib continuously about a lower end of the housing.

The thin-walled sections or membranes can be recessed from, extend between and extend contiguous to the ribs such that the thickness of the frame is greater than the thickness of the panels.

The ribs and panels or membrane in combination allow for the menstrual collection device to hold its shape and collect fluid while still being able to be folded to reduce the surface area of the collection device (e.g., the collection device can be folded to be as thin as a tampon) and fit inside the applicator. As will be described below, the ribs, sidewalls and/or base allow for a force applied to the collection device from the applicator to translate from the ribs, sidewalls and/or base to the rim of the collection device to ensure the cup fully opens and stays fully opened in an inserted/installed state.

The rim and a sidewall of the collection device that includes the frame and the panels can extend in a sloped manner such that the rim is a first height at a first side of the menstrual collection device and a second height, which is greater than the first height, at a second side of the menstrual collection device.

In an embodiment, the applicator comprises a housing that includes a sidewall that is delimited at a first end by a tip and a second end by a base, and a plunger that is arrangeable within the cavity of the housing. The housing can include a first and second surface with the second surface defining a cavity that extends within the housing from the base to the tip. The applicator is configured to allow for menstrual collection device to pass therein while applying a force to the base, sidewalls and/or rib of the menstrual collection device as the collection device exits the tip of the applicator that translates to the rim to aid the menstrual collection device to deploy to a fully open state without the need for a user to adjust the collection device within the vaginal canal or with minimal adjustment, if needed.

The tip of the housing can have a plurality of projections or flaps that extend in a curved manner from the sidewall toward an apex of the tip. The projections can be spaced from each other by gaps that extend into an opening at an end of each of the projections. The ends of each of the projections can be rounded. The base of the housing can have a cylindrical shape that flares outwardly from the sidewall of the housing such that an outer periphery of the base has a greater circumference than a circumference of the first surface of the sidewall of the housing.

The sidewall of the housing can be comprised of a first material and the projections of the housing can be comprised at least in part of a second material that is different from the first material with the second material having a modulus of elasticity that is greater than that of the first material. That is, at least the second material can have elastomeric properties such that the projections are flexible in an outward direction when a force is applied thereto to expand the opening at the tip and automatically and return to their original resting state or closed position when the force is no longer applied thereto.

The plunger can include a cylindrical main body that extends between a first end and a second end with the overall length being greater than the cavity of the applicator housing. The first end including a cavity that extends from the first end of the plunger toward the second end thereof and the second end defined by a base that has an outer periphery that is greater than an outer periphery of the main body and configured, in conjunction with the base of the housing, to act as a stop to limit movement of the plunger within the cavity of the housing.

In another embodiment, the present disclosure is directed to a method of inserting a menstrual collection device into a vaginal canal. The method can comprise the following steps: providing a menstrual collection device comprising a housing that is open at a first end and tapers to a base at a second end from which a stem extends, the housing defines a cavity therein and includes a frame having a first thickness, panels having a second thickness extending between the frame and a rim extending from the frame to delimit the first end; providing an applicator comprising a housing including a sidewall that is delimited at a first end by a tip and a second end by a base, and the housing having a first surface and a second surface with the second surface defining a cavity that extends within the housing from the base to the tip and a plunger that is arrangeable within the cavity of the housing; folding the menstrual collection device; arranging the menstrual collection device that is folded within the cavity of the housing of the applicator; inserting the plunger within the cavity of the applicator; inserting the applicator within a vaginal cavity; moving the plunger towards the tip of the housing of the applicator such that the applicator contacts the menstrual collection device and the menstrual collection device contacts the projections of the housing of the applicator; and pushing the plunger with a force applied thereto that causes the projections to move outwardly and beyond the first surface of the housing, at least in part, to expand an opening at the tip of the housing of the applicator and allow the menstrual collection device to pass through the opening while applying a force to the collection device to cause the menstrual collection device to expand from being folded to a fully open state within the vaginal canal.

DETAILED DESCRIPTION OF EMBODIMENTS OF THE PRESENT DISCLOSURE

With reference now to the drawings and in particular FIGS. 1-28, embodiments of a menstrual collection device and an applicator and related features thereof will be described.

Figure 1:
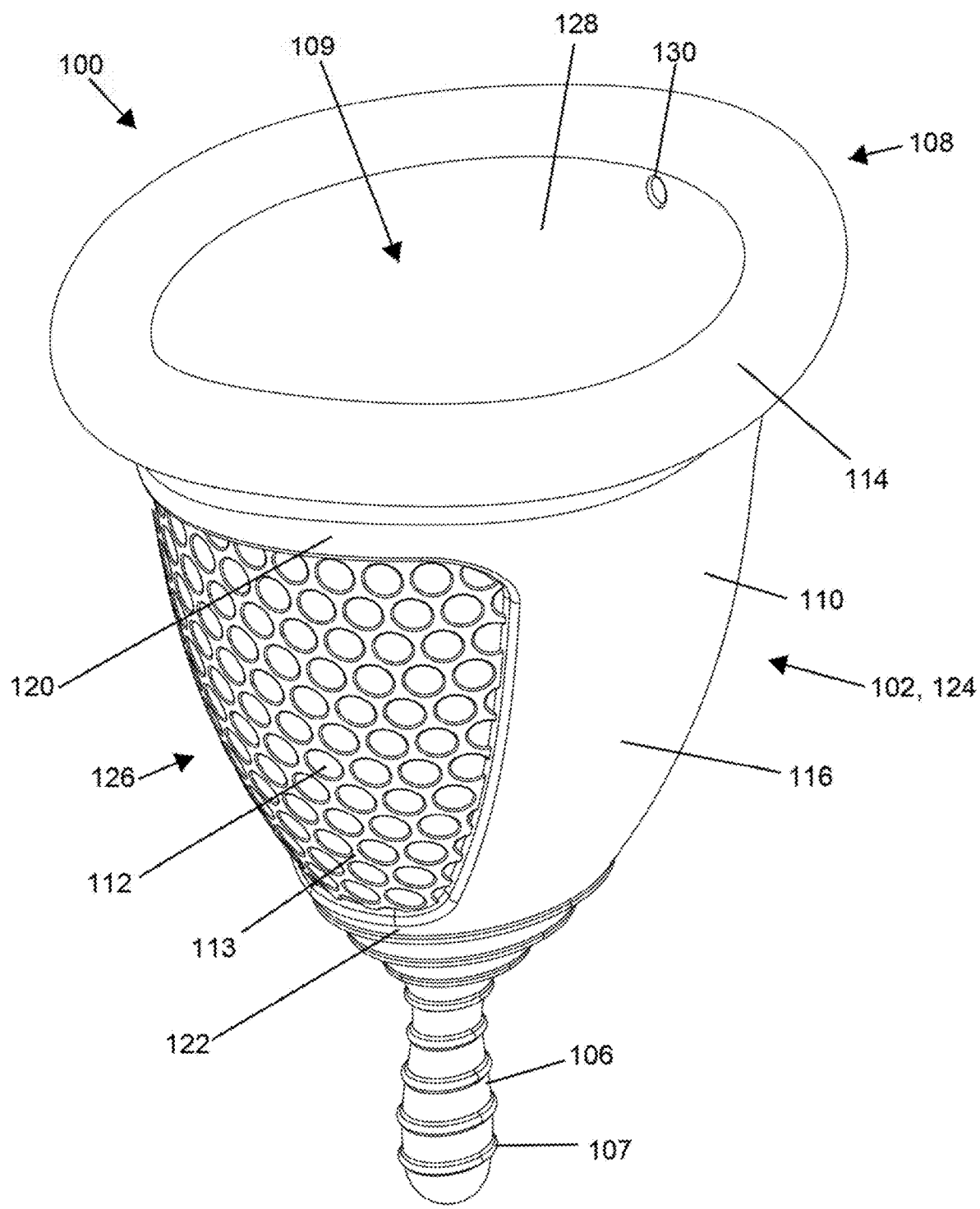
FIG. 1 is a perspective view of a menstrual collection device according to an embodiment of the present disclosure.
Figure 3:
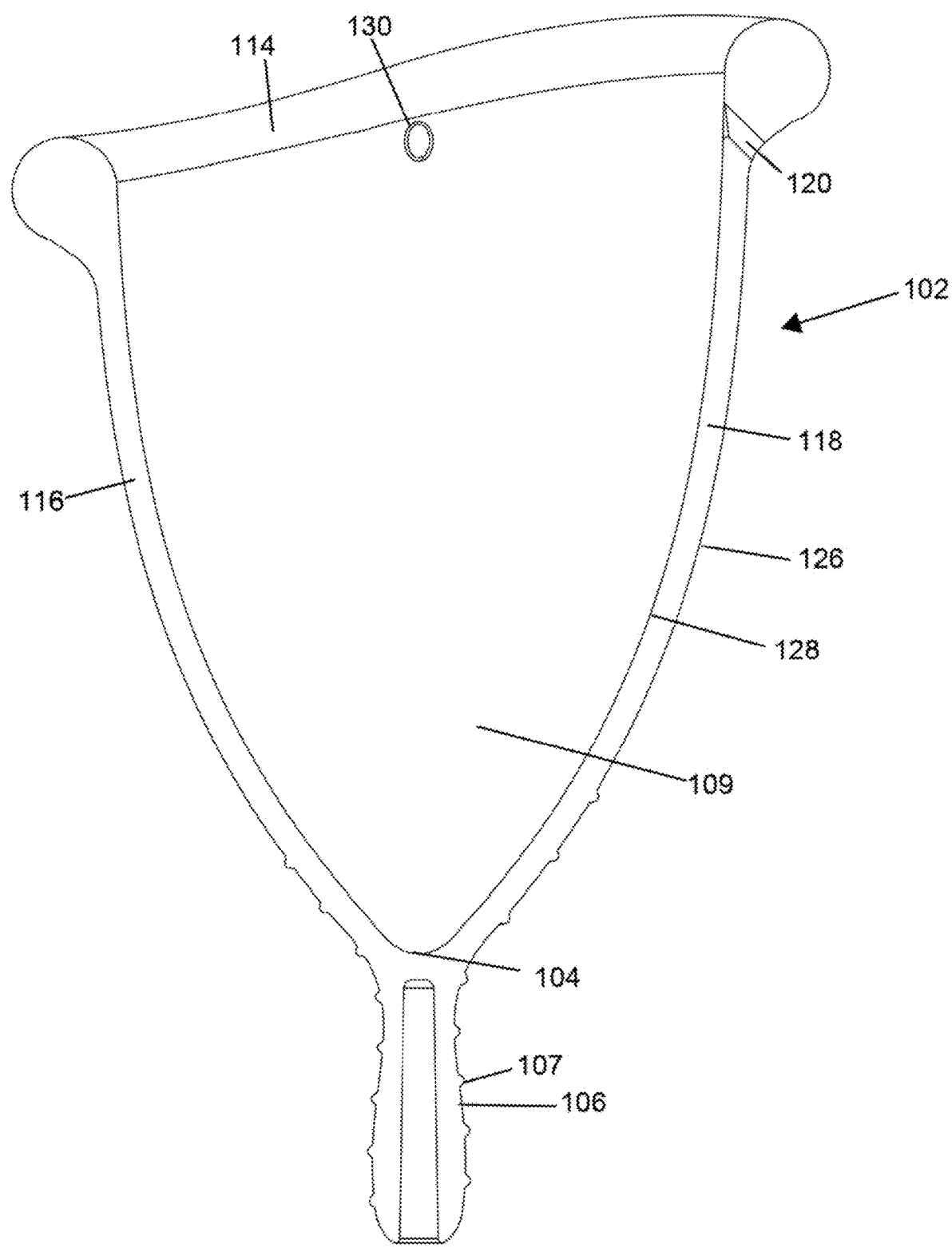
FIG. 3 is a cross-sectional view taken along line A-A of FIG. 2.

FIG. 1 illustrates a menstrual collection device 100, which can be a cup that can be, for example, bowl-shaped, bell-shaped or the like, according to an embodiment of the present disclosure that generally includes a housing 102 that tapers to a base 104 (see FIG. 3) from which a stem 106 extends. The housing 102, which defines a cavity 109 therein that is delimited at an open end 108, is comprised of thick-walled sections or walls that have a first thickness defined by a frame/cage 110, thin-walled sections or walls that have a second thickness defined by a support panel or membrane 112 and a rim 114. The frame 110 includes a first rib or panel 116, a second first rib or panel 118, a third first rib or panel 120 and a fourth first rib or panel 122. The ribs or panels 116, 118, 120, 122 all extend contiguous to each other with the first rib 116 and the second rib 118 spaced approximately 180 degrees from each other and extending vertically about the housing 102, the third rib 120 extending from a distal end of each of the first rib 114 and the second rib 116 continuously about an upper end of the housing 102 and the fourth rib 122 extending from a proximal end of each of the first rib 116 and the second rib 118 continuously about a lower end of the housing 102 and contiguous to the stem 104. As can be seen in FIG. 3, the first rib 114 and the second rib 116 are substantially the same thickness as each other. The stem 106 can include ridges 107 that are spaced from each other and extend thereabout.

Figure 2:
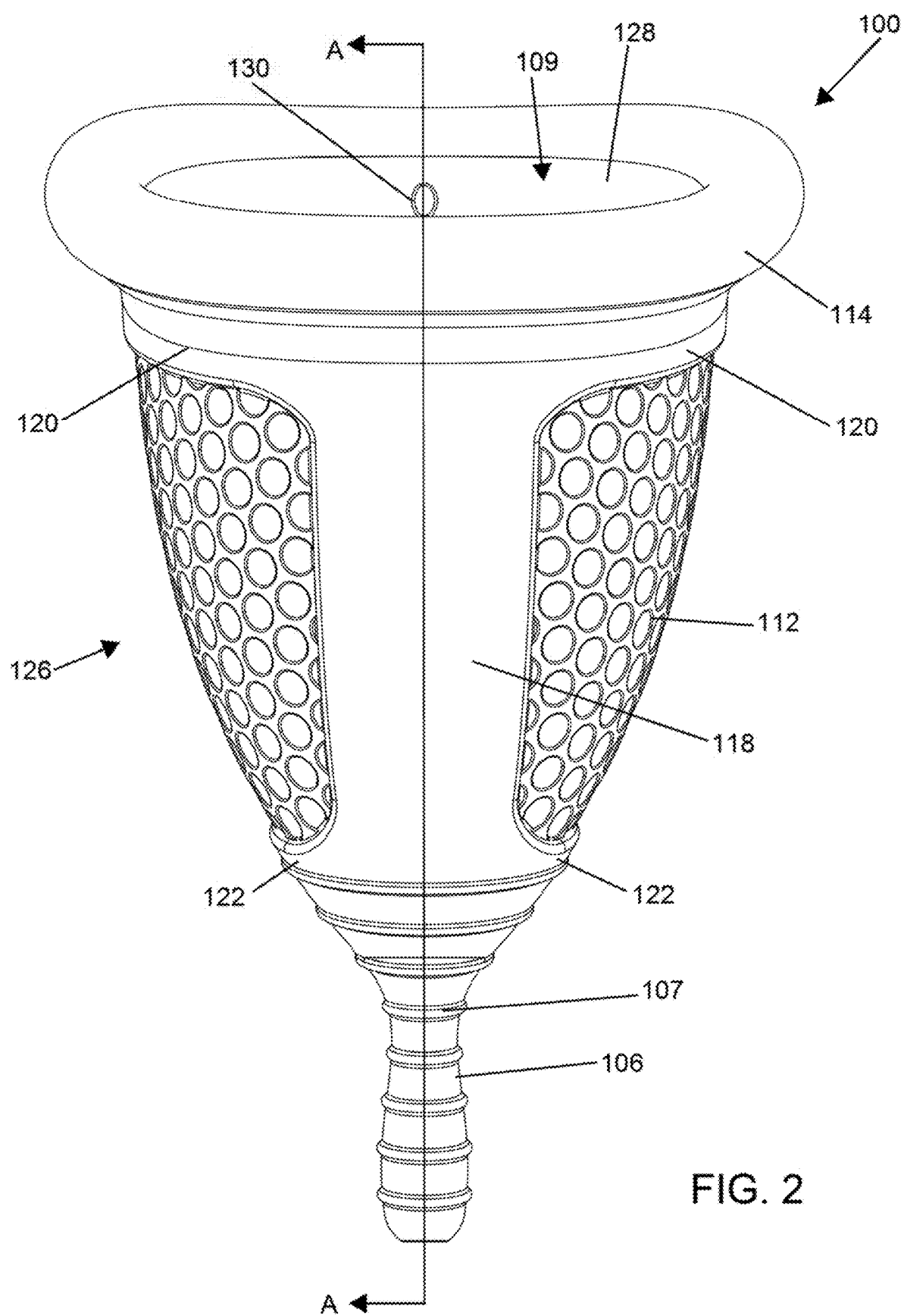
FIG. 2 is a side view the menstrual collection device of FIG. 1.
Figure 4:
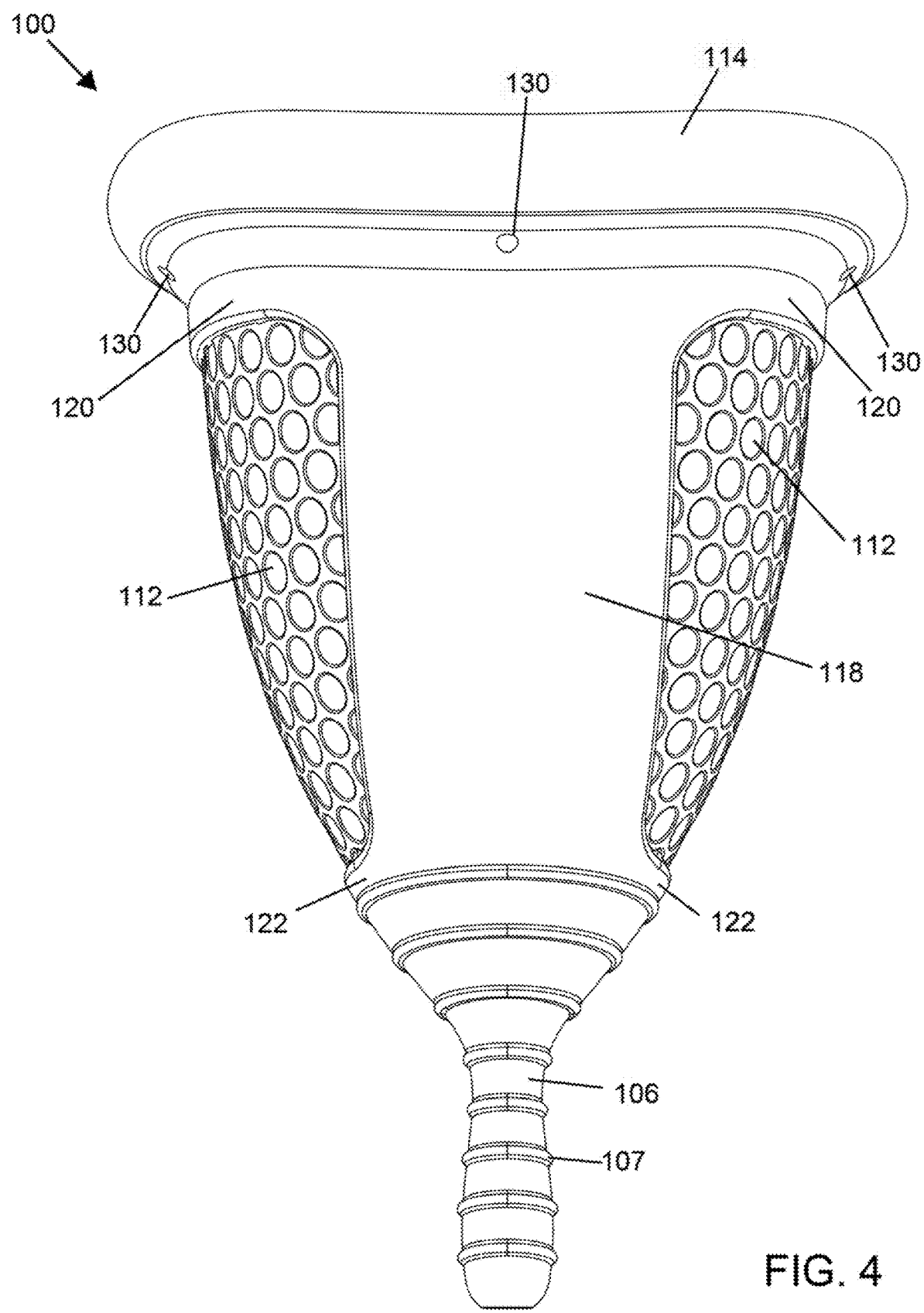
FIGS. 4-6 are additional side views the menstrual collection device of FIG. 1.
Figure 5:
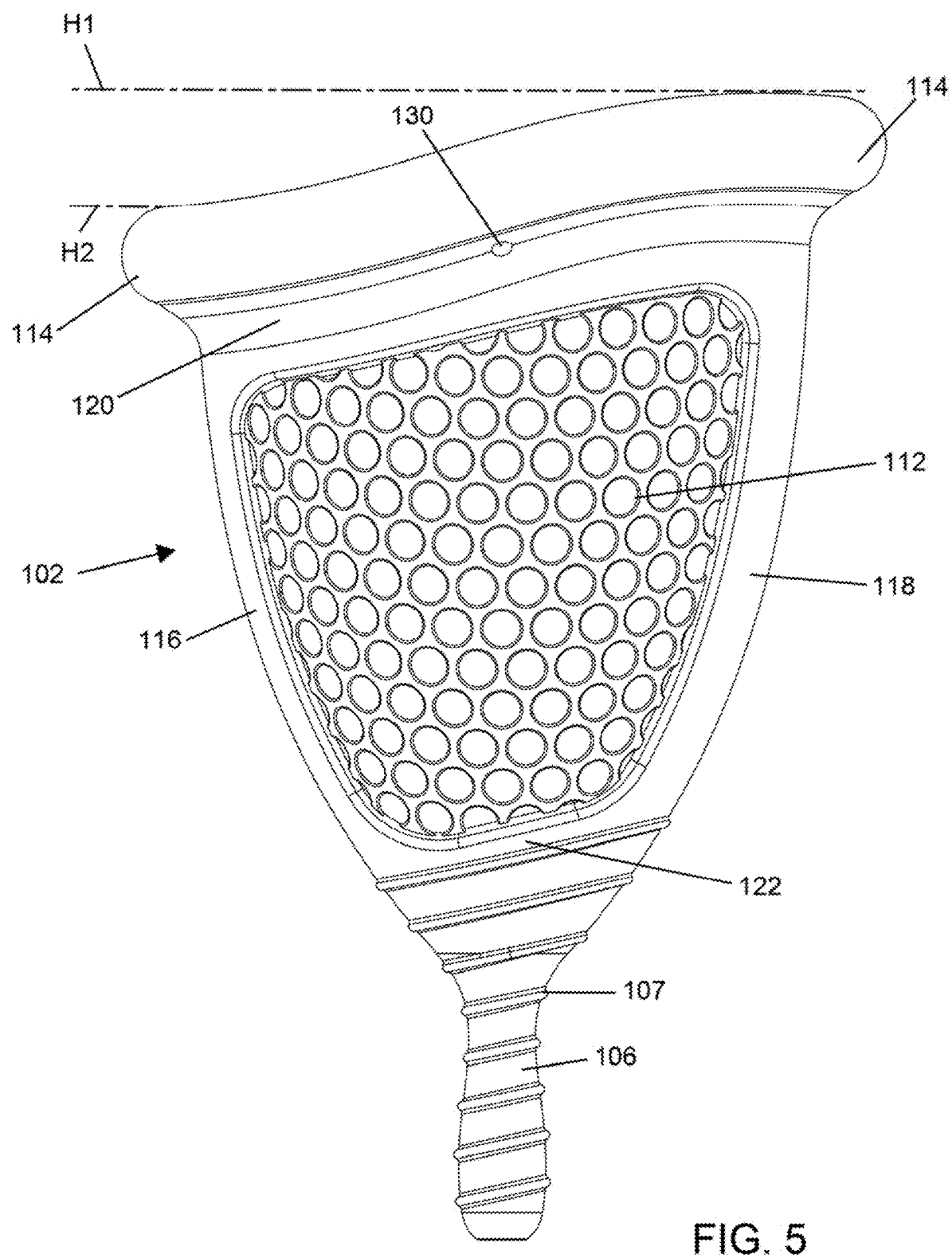
Figure 6:
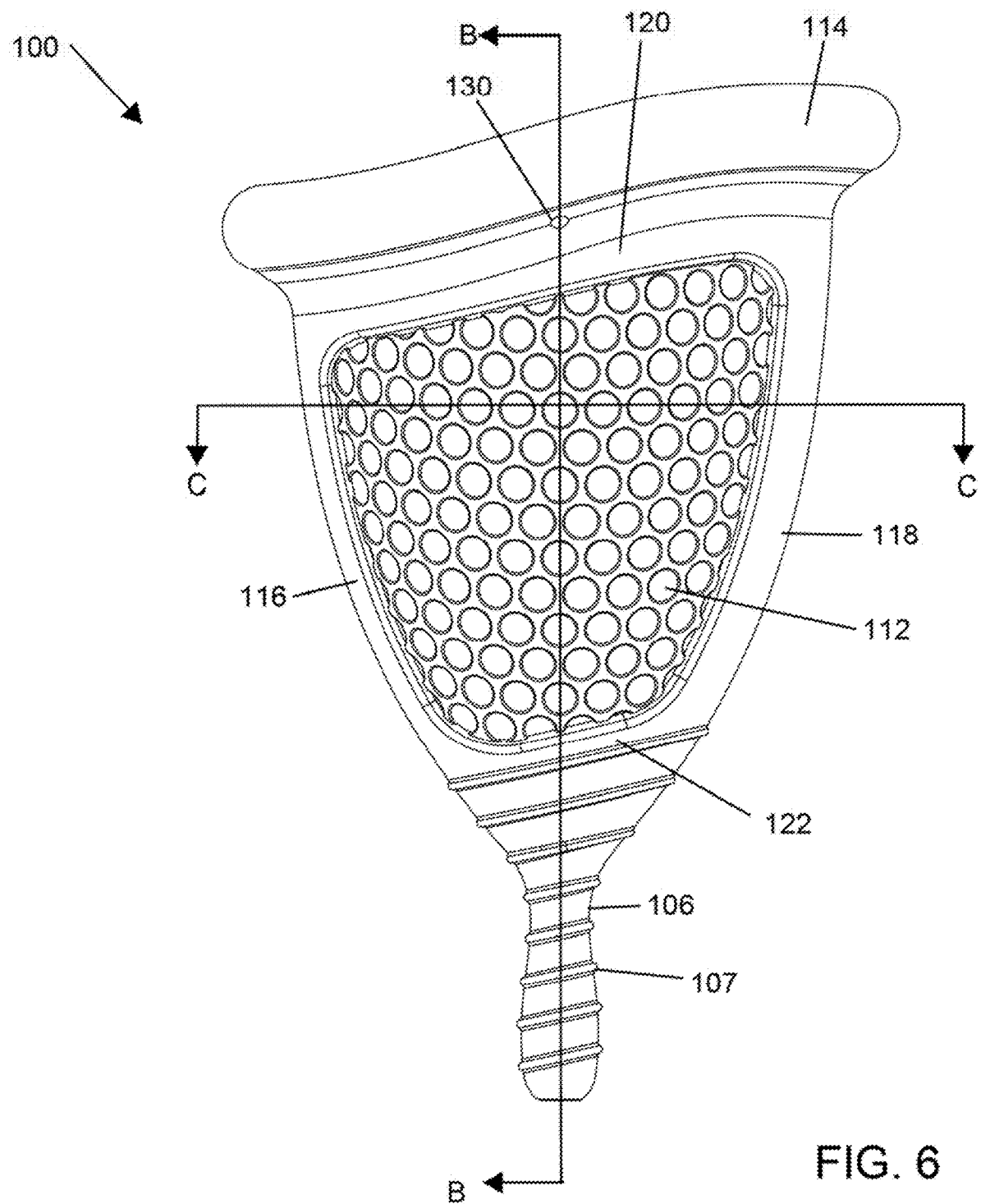
Figure 7:
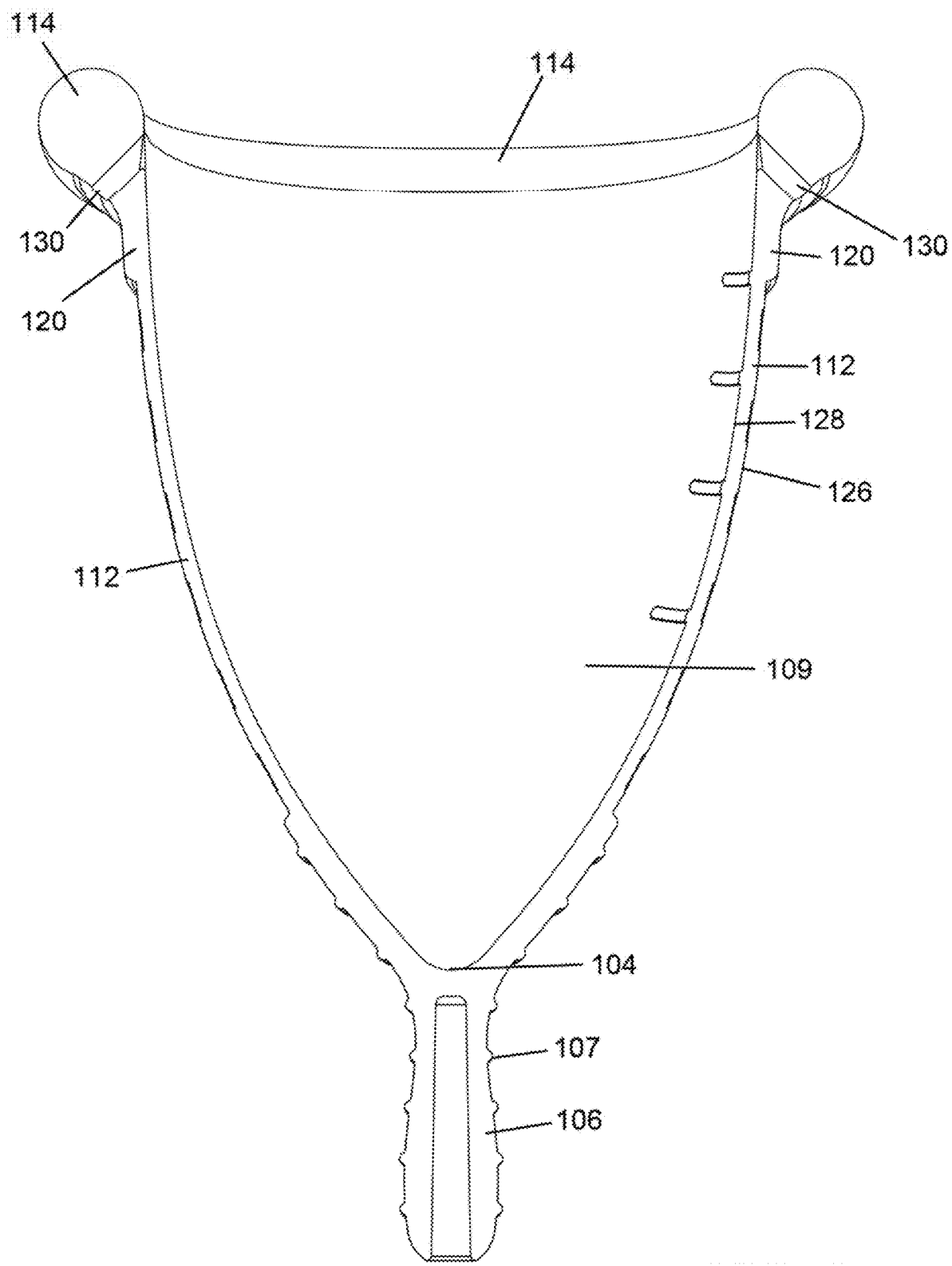
FIG. 7 is a cross-sectional view taken along line B-B of FIG. 6.
Figure 8:
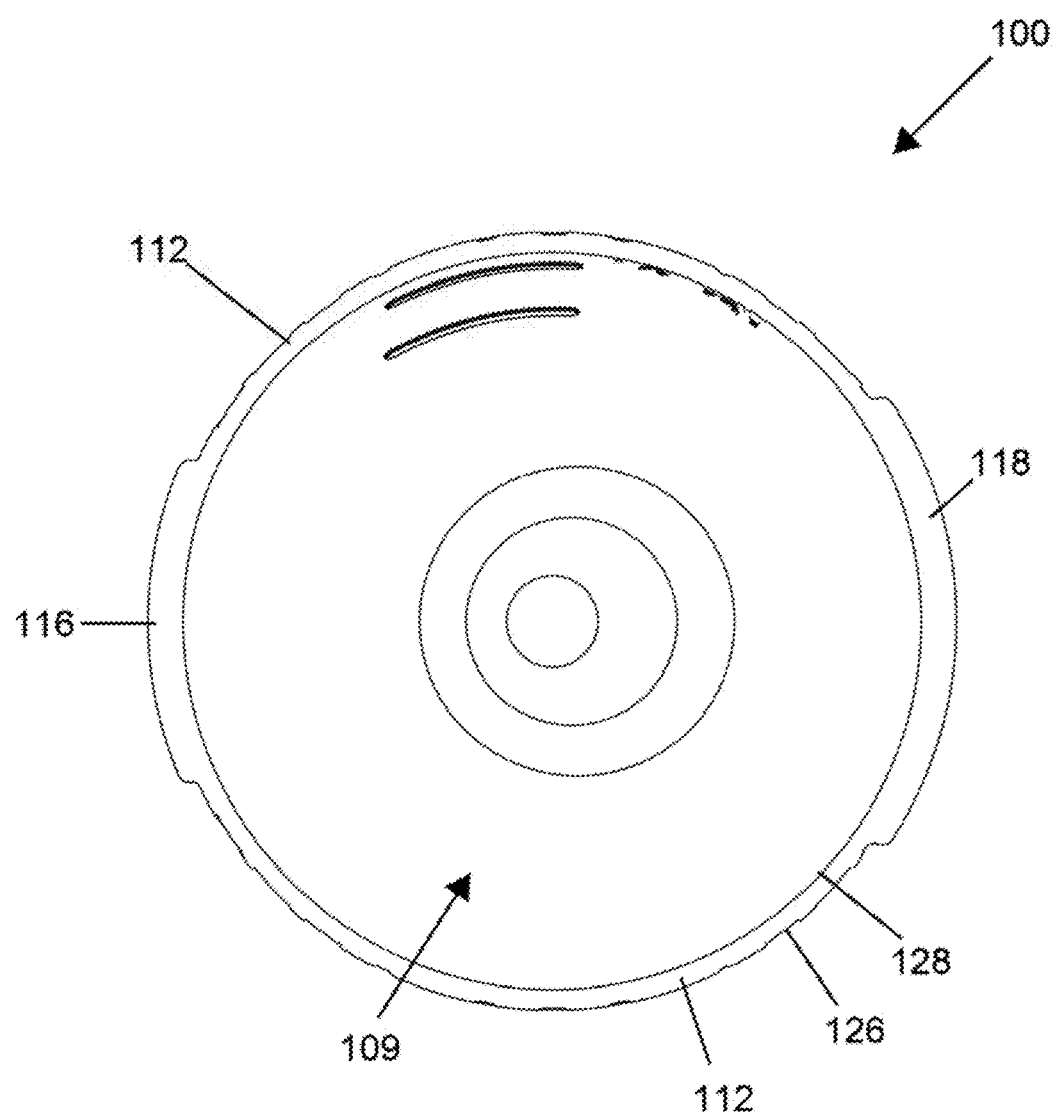
FIG. 8 is a cross-sectional view taken along line C-C of FIG. 6.
Figure 9:
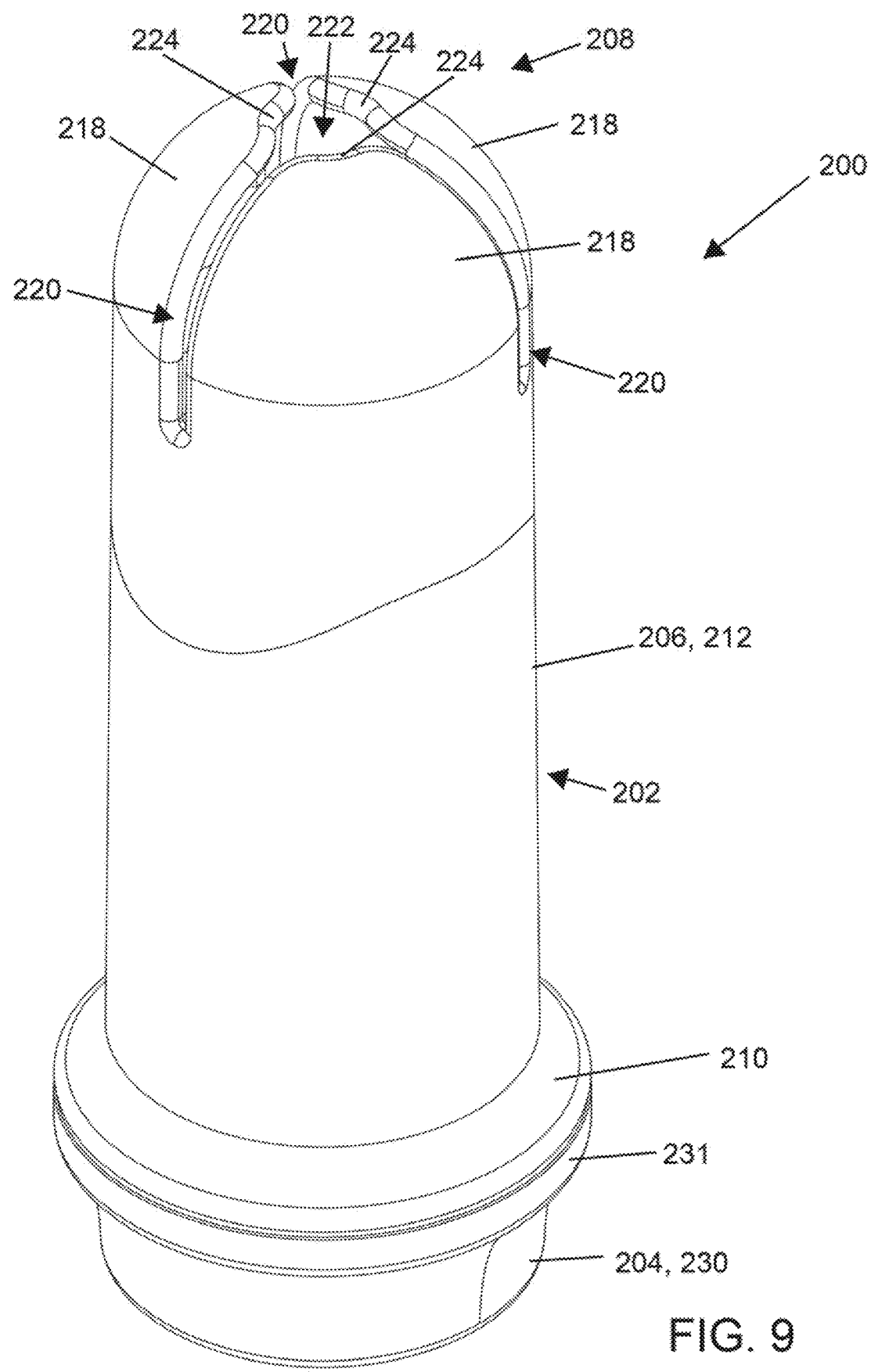
FIGS. 9 and 10 are perspective views of an applicator according to an embodiment of the present disclosure.
Figure 10:
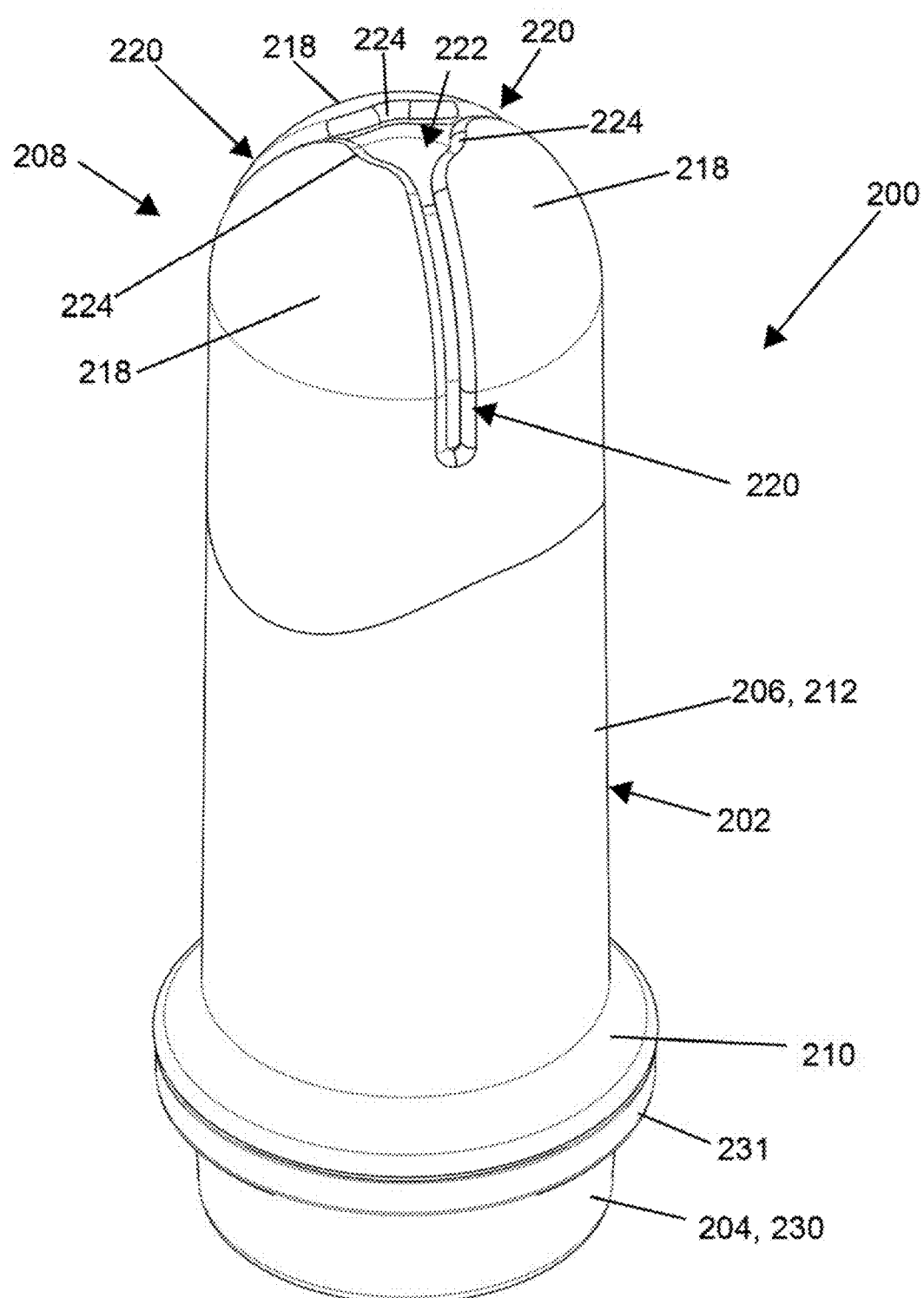
Figure 11:
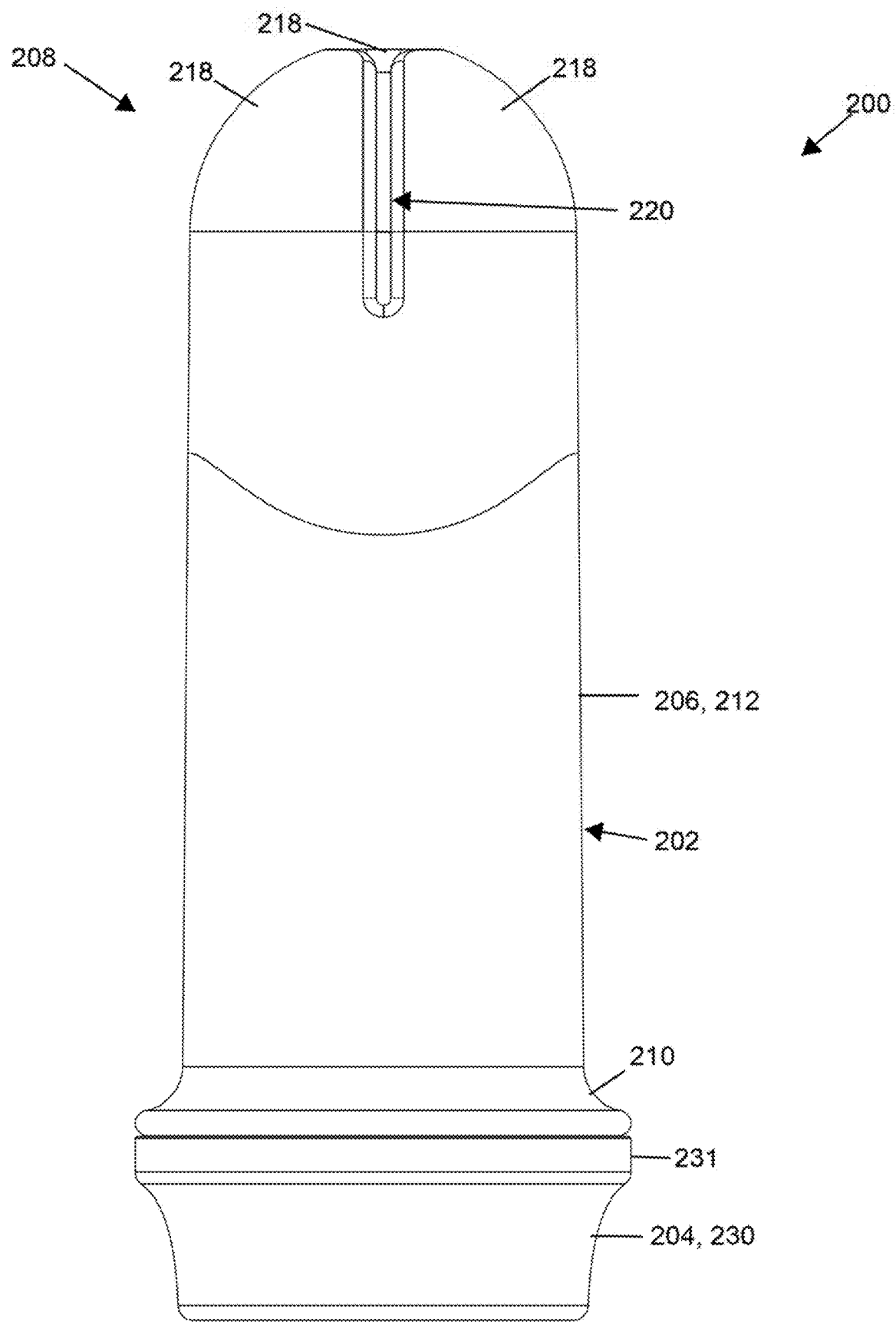
FIGS. 11 and 12 are side views of the applicator of FIGS. 9 and 10.
Figure 12:
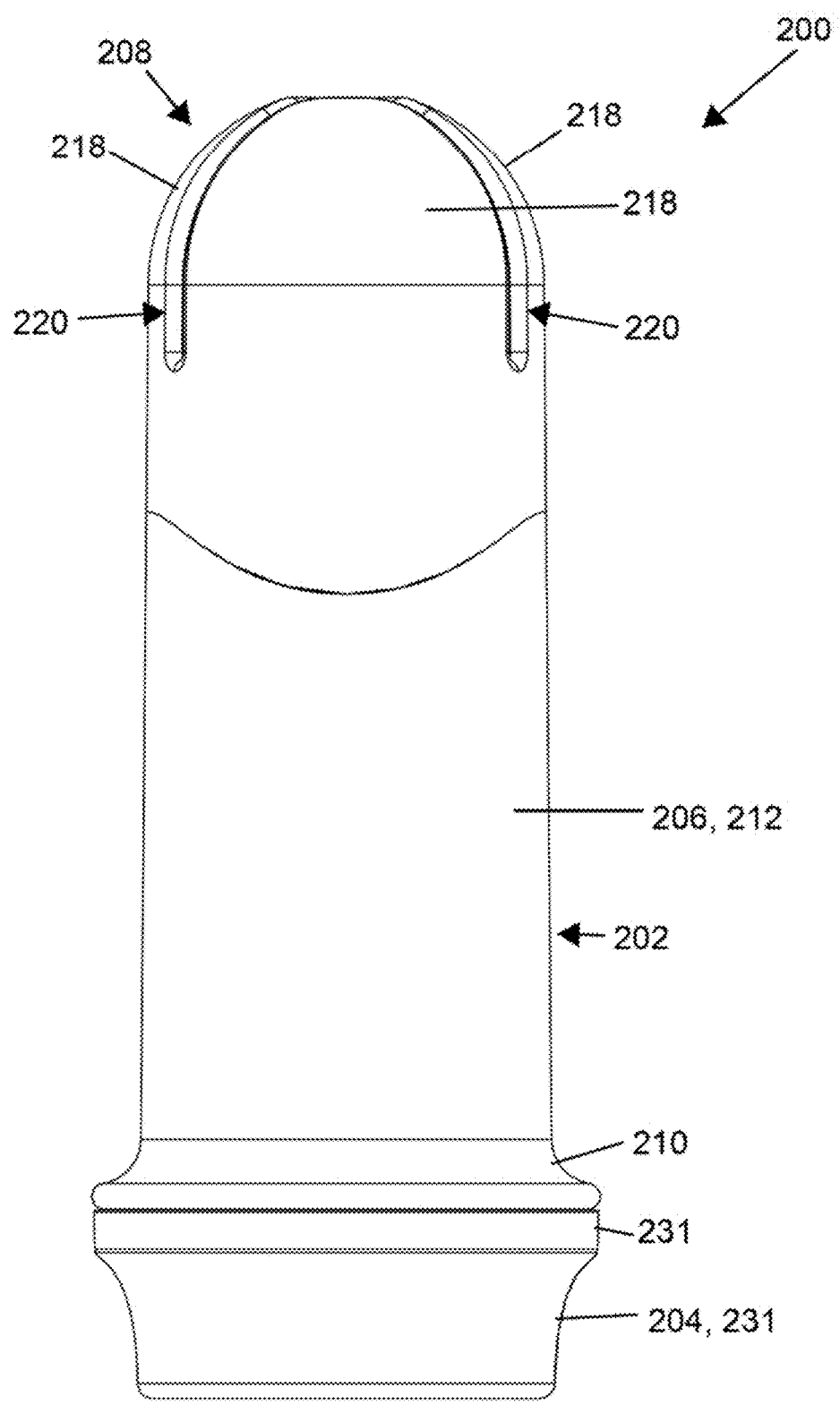
Figure 13:
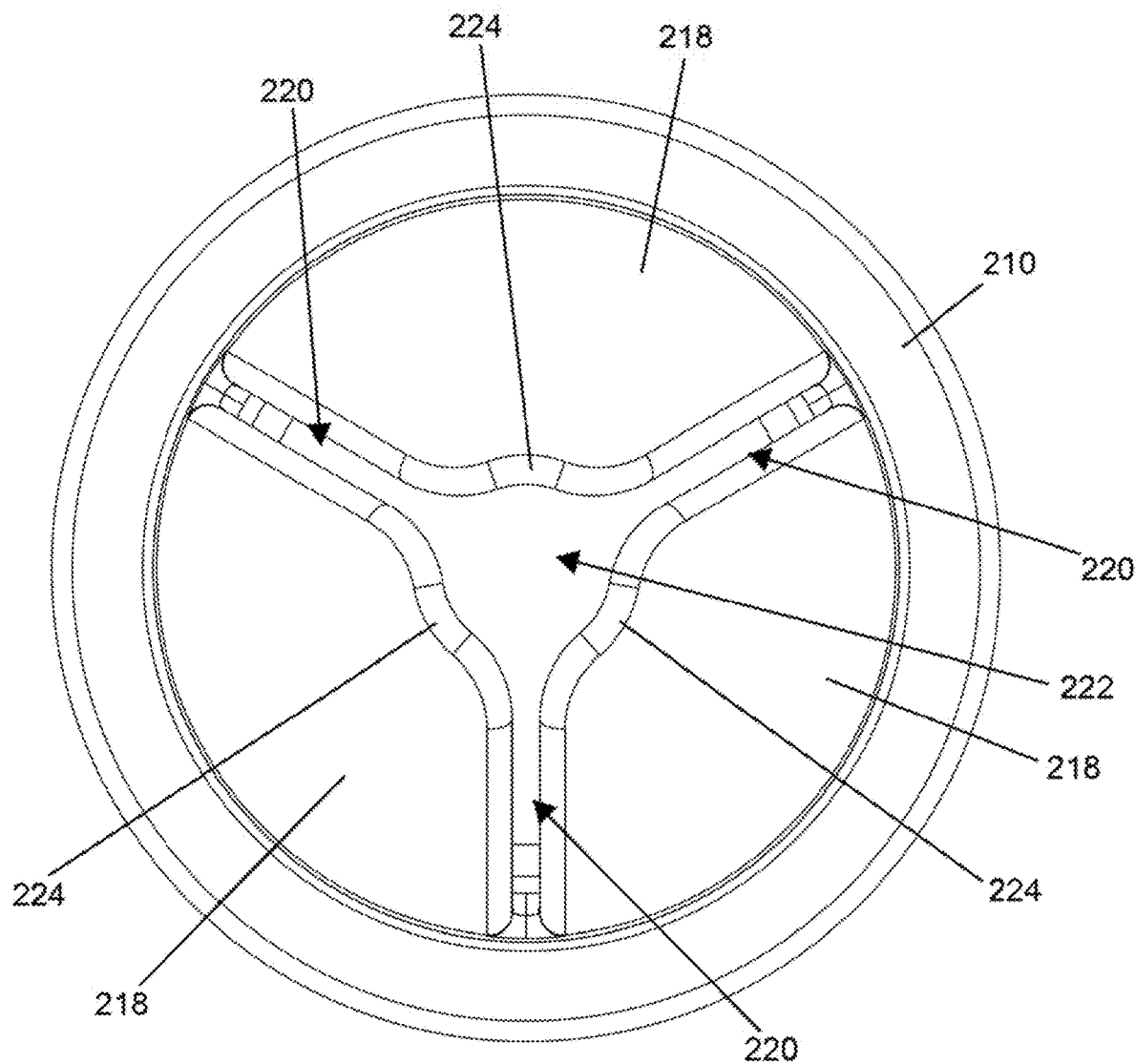
FIG. 13 is a top view of the applicator of FIGS. 9 and 10.
Figure 14:
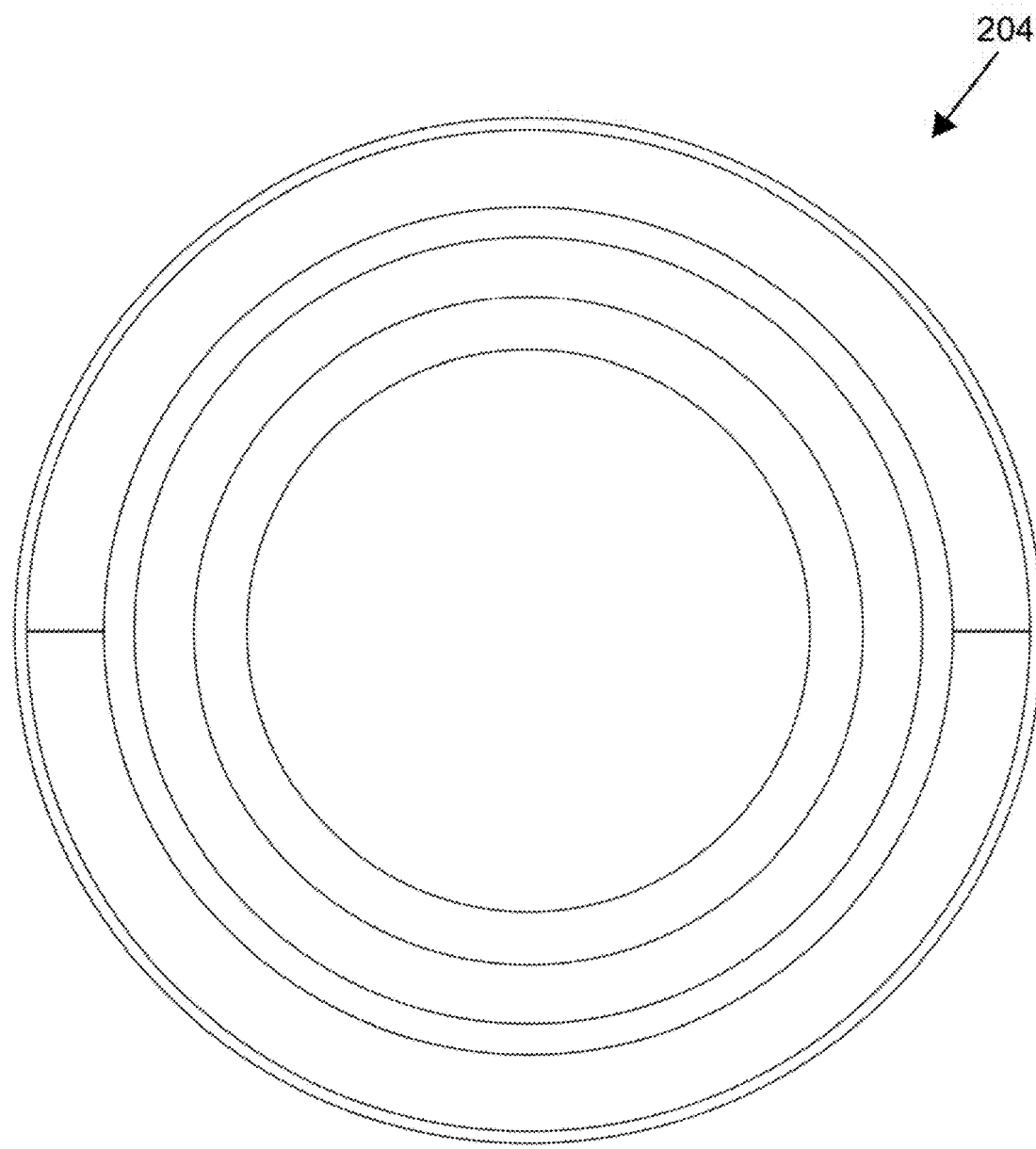
FIG. 14 is a bottom view of the applicator of FIGS. 9 and 10.

As can be seen, for example, in FIGS. 2, 4 and 7, the support panels or membrane 112 have a thickness that is less than the thickness of the ribs 116, 118, 120, 122 and as a result forms recessed sections between the ribs 116, 118, 120, 122. Thus, the collection device 100 includes a first thickness at the ribs 116, 118, 120, 122 and a second thickness at the support panels or membrane 112, which is thinner than the thickness of the ribs 116, 118, 120, 122. Together the ribs 116, 118, 120, 122 and the support panels or membrane 114 define a sidewall 124 of the housing 102. The sidewall 124 includes an outer surface 126 and an inner surface 128. While the support panels or membrane 112 is depicted in the figures with a repeating circular pattern 113, the membrane can include any pattern that is known or may become known or no pattern at all.

In an embodiment of the present disclosure, the first thickness is about 1.5 mm and the second thickness is about 0.75 mm, providing a ratio of a thickest portion of the housing 102 and a thinnest portion of the housing 102 of about 2 mm (1.5 mm/0.75 mm). Alternatively, according to other embodiments, the first thickness can be, for example, 1.0 mm, 1.2 mm, 1.3 mm, 1.4 mm, 1.5 mm, 1.6 mm, 1.7 mm, 1.8 mm, 1.9 mm, etc., the second thickness can be, for example, 0.4 mm, 0.5 mm, 0.6 mm, 0.7 mm, 0.8 mm, 0.9 mm, 1.0 mm, 1.1 mm, 1.2 mm, 1.3 mm, etc. and ratios of a thickest and thinnest portions of the housing 102 are about 1.2, 1.4, 1.6, 1.8, 2.2, 2.4, 2.6, 2.8, 3.0, 3.5, 4.6, etc.

The inner surface 128 defines a period fluid collection volume of 25 ml, providing a ratio of the period fluid collection volume to a thinnest portion of the housing 102 of about 31,000 $mm^2$ (25 ml/0.75 mm). Other period fluid collection volumes may be provided, such as 10 ml, 15 ml, 20 ml, 30 ml, 35 ml, etc. and ratios of the period fluid collection volume to a thinnest portion of the housing 102 of about 13.00 $mm^2$, 15,000 $mm^2$, 20,000 $mm^2$, 35,000 $mm^2$, 40,000 $mm^2$, 50,000 $mm^2$, etc.

While the cavity 109 that is defined by the inner surface 128 can hold roughly 25 ml of fluid, the representative embodiments should not be limiting with respect to the volume of liquid that can be held by the collection device 100. The collection device 100 can be sized to hold any amount of liquid desired. For example, the cavity 109 could be smaller to hold 5 ml of fluid or larger to holder 30 ml of fluid.

The rim 114 extends from the third rib 120 and delimits the open end 108 of the collection device 100. As can be seen, for example, in FIGS. 2-6, the rim 114 and sidewall 124 of the collection device 100 extends in a sloped manner such that the rim 114 extends a first height H1 at a first side of the collection device 100 and a second height H2, which is greater than the first height H1, at a second side of the collection device 100. The difference in height reduces the overall surface area of the collection device 100, which allows the collection device 100, when folded, to be thinner and easier to insert into an applicator or vaginal canal.

As can be seen in FIGS. 1-6, holes 130 extend through the sidewall 124 of the collection device 100 between the outer surface 126 and the inner surface 128 thereof and in particular through the third rib 120. The through holes 130 are configured to allow air into the menstrual collection device 100 when the collection device 100 is initially inserted into the vaginal canal to assist in the opening of the menstrual collection device 100 from a folded position. When a user wants to remove the menstrual collection device 100, the holes 130 assist in breaking the seal formed between the menstrual collection device 100 and vaginal canal by allowing air in the collection device 100 to be displaced by collected menstrual fluid.

The menstrual collection device 100 can be comprised of silicone or another medical grade material that allows for flexibility and bending to permit the collection device to be folded while at the same time having elastomeric properties to return to an original, fully open state when the collection device is not being compressed and/or folded.

FIGS. 9-16 illustrate various views of the applicator 200 that includes a housing 202 and a plunger 204. The applicator 200 can be comprised, for example, of plastic or similar material.

The housing 202 includes a cylindrical sidewall 206 that is delimited at a first end by a tip 208 and at a second end by a base 210. The sidewall 206 includes an external surface 212 and an internal surface 214 with the internal surface 214 defining a cavity 216 that extends within the housing 202 from the base 210 to the tip 208.

The tip 208 has a hemispherical shape that is defined by a plurality of flexible projections or flaps 218 that extend in a curved manner from the sidewall 206. As shown, the projections 218 extend directly from the sidewall 206. The projections or flaps 218 are spaced from each other by gaps 220 that extend into an opening 222 at the distal end of the housing 202. The flaps 218 each extend from the sidewall 206 of the housing 202 and include rounded edges 224 that delimit each of the projections or flaps 218. While three flaps are shown, it is noted that any number of flaps can extend from the sidewall of the housing to define the tip.

The projections or flaps 218 are comprised, at least in part, of a material that has elastomeric properties to allow for flexibility of the projections or flaps 218 in an outward direction to expand the opening at the tip 208, when a force is applied thereto, to allow a menstrual collection device 100 to pass through the tip 208. As the menstrual collection device 100 passes through the opening 222, the projections or flaps 218 apply a force on the base 104, sidewalls 128 and/or ribs 116, 118, 120, 122, which translates to the rim 114, causing the rim 114 to expand from a folded state to a fully open state to create a seal with the vaginal cavity without the need to substantially adjust the collection device 100. Once a force is no longer applied to the projections or flaps 218 to push the menstrual collection device 100 therethrough, the projections or flaps 218 automatically and instantly return to their original resting state or closed position.

A combination of the durometer, material and geometry of the tip 208 allow for the menstrual collection device 100 to pass therethrough and for the tip 208 of the applicator 200 to return to the closed state once the collection device 100 passes therethrough.

As illustrated in FIGS. 9-13 and 15A, the base 210 of the applicator 200 has a cylindrical shape that flares outwardly such that the outer periphery of the base 210 is wider than the circumference of the external surface 212 of the sidewall 206 of the housing 202.

Figures 15A, 15B:
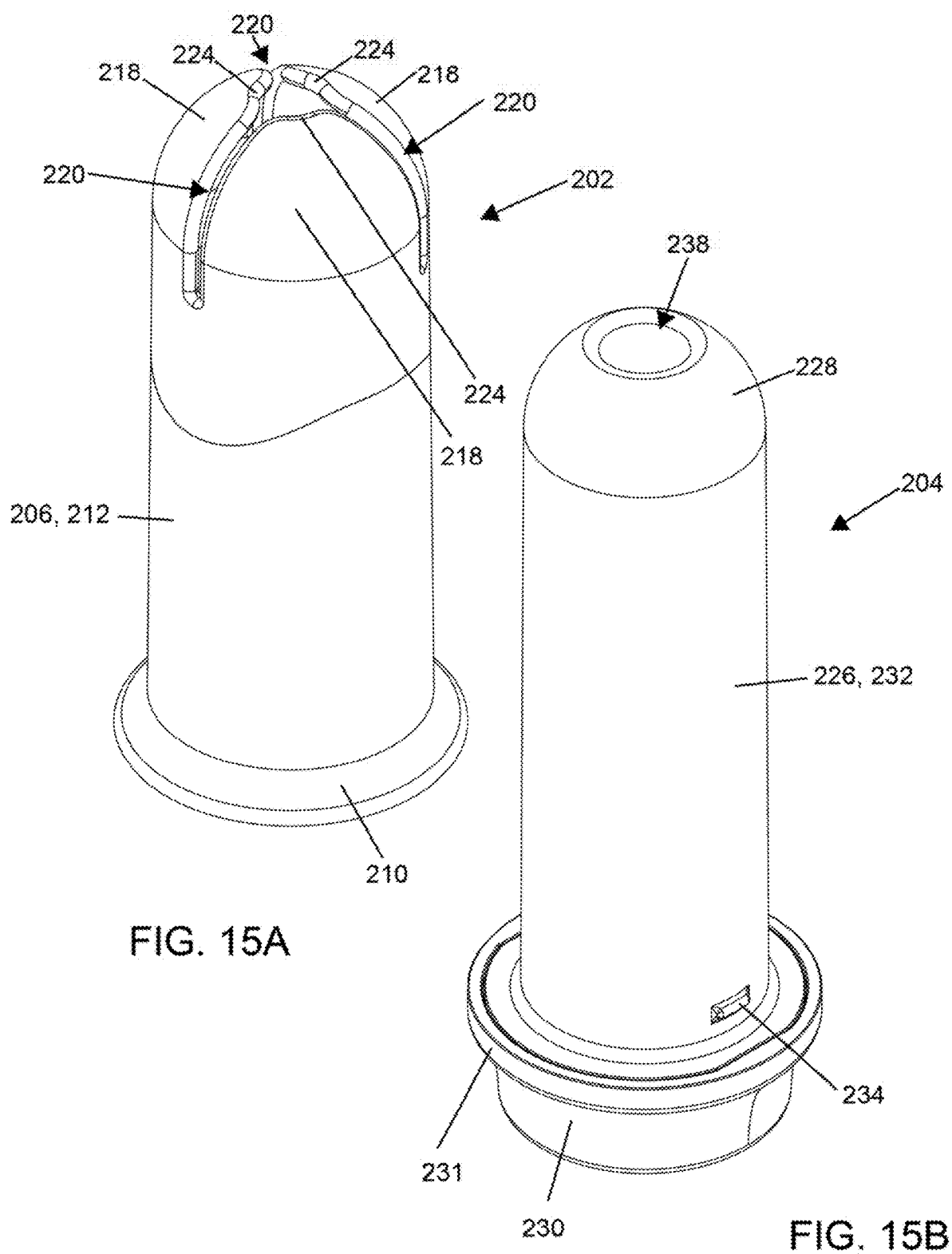
FIGS. 15A and 15B are perspective views of the applicator housing and the plunger of the applicator of FIGS. 9 and 10.
Figure 16A:
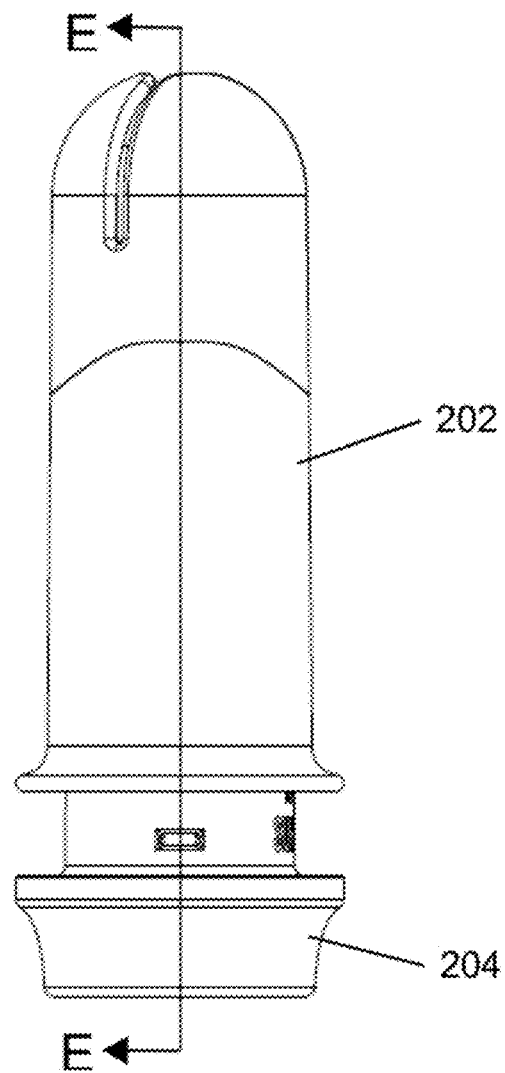
FIG. 16A is a perspective view of the applicator housing and plunger partially spaced from each other.
Figure 16B:
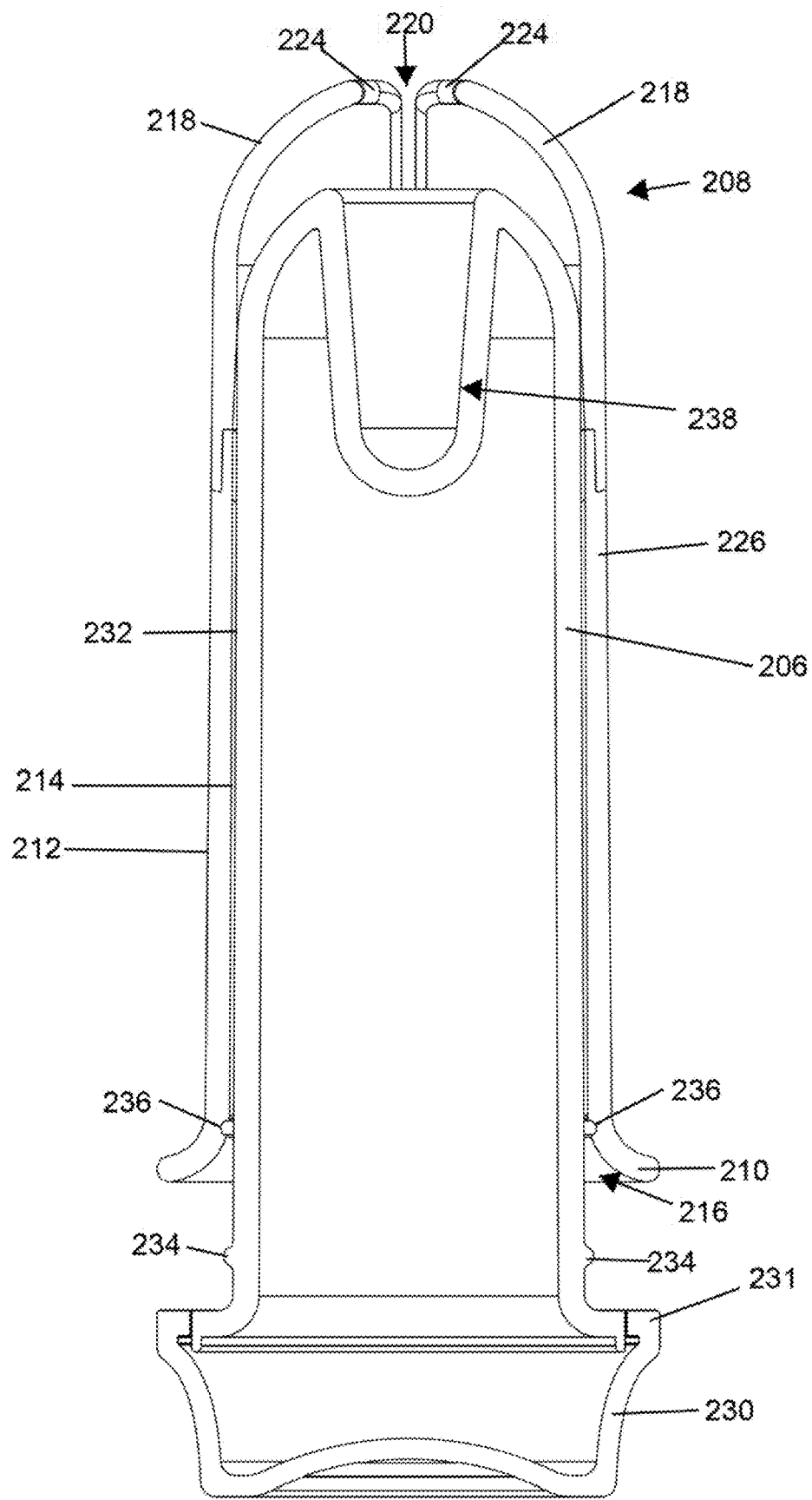
FIG. 16B is a cross-sectional view of FIG. 9 taken along line D-D depicting the plunger substantially nested within the applicator body.
Figure 17:
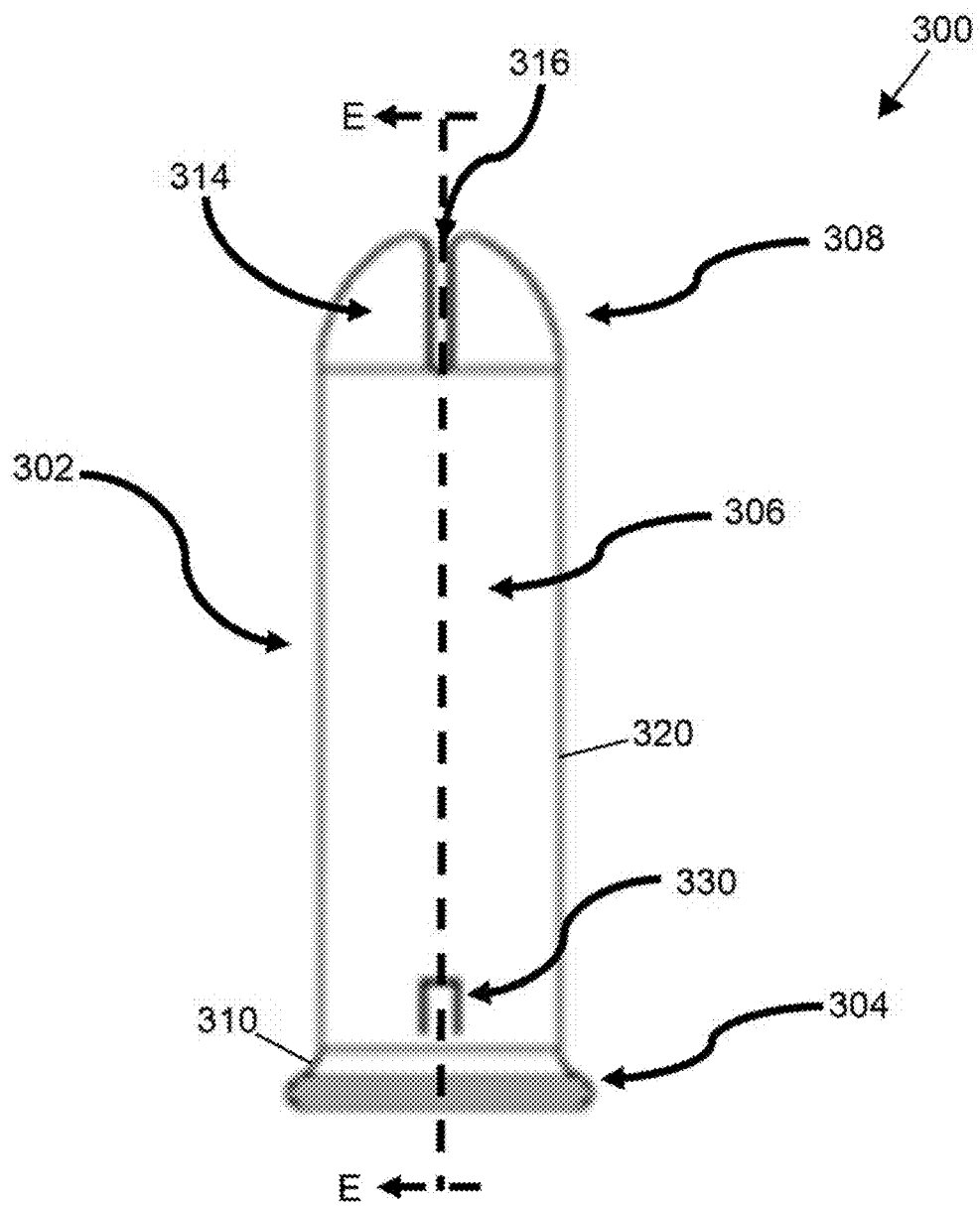
FIG. 17 is a side view of an applicator according to an embodiment of the present disclosure.

The plunger 204 as can be seen, for example, in FIGS. 15B and 16, includes a cylindrical main body 226 that is delimited at one end by a tip 228 and a second, opposite end by a base 230. An outer surface 232 of the main body 226, which extends linearly between the tip 228 and the base 230, includes projections 234 that interact with recesses 236 that extend from the inner surface 214 of the sidewall 206 of the housing 202 towards the outer surface 212 thereof. The base 230 has a rim 231 that defines an outer circumference that is greater than that of the main body 226 for the base 210 of the housing 202 of the applicator 200 to interact therewith.

The plunger 204 has a length such that the plunger 204 extends beyond the distal end of the housing 202 of the applicator 200 tip when the plunger is fully inserted within the housing 202 of the applicator 200. By extending the plunger 204 beyond the tip of the housing 202, which greatly improves the success rate of deployment of the collection device 100 to a fully open state.

As shown in FIG. 16, a cavity 238 extends from the tip 228 of the plunger 204 towards the base 230 thereof. The cavity 238 can have a collection device-like shape to support at least a portion of the menstrual collection device 100, such as at least a portion of the base 104 and the stem 106, to reduce the likelihood that the menstrual collection device 100 will become pinched or trapped between the inner surface 214 of the sidewall 206 of the applicator 200 and the external surface of the plunger 204 as the menstrual collection device 100 is being pushed within the applicator housing 202 by the plunger 204. The cavity 238 also reduces the surface area of the collection device 100 that interacts with the inner surface 214 of the sidewall 206 of the housing 202 and in turn, reduced the friction between the menstrual collection device 100 and the inner surface 214 of the sidewall 206 of the housing 202.

FIGS. 17-22 depict another embodiment of an applicator 300 that generally includes a housing 302 and a plunger 304. The applicator 300 can be comprised, for example, of a plastic or similar.

Figure 20:
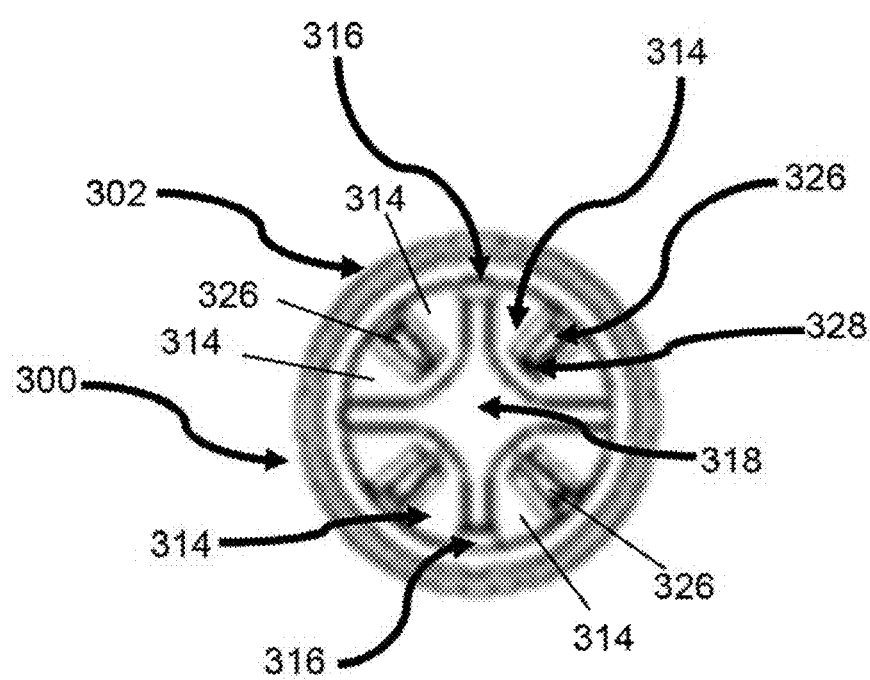
FIG. 20 is a bottom view of the applicator of FIG. 17.

The housing 302 includes a sidewall 306 that is cylindrical and is delimited at a first end by a tip 308 and at a second end by a base 310. A cavity 313 extends within the housing 302 from the base 310 to the tip 308. The tip 308 has a hemispherical shape that is divided into a plurality of substantially equivalent projections or flaps 314 with gaps 316 that extend therebetween. As shown in FIG. 20, the projections or flaps 314 each have rounded edges 317 and extend from the sidewall 306 of the housing 302 and form an opening 318 at a distal end between the projections or flaps 314. While four flaps or projections 314 are shown, the number of projections or flaps that extend from the sidewall of the housing 302 to define the tip 308 can be more or less than the four depicted.

The projections or flaps 314 are comprised, at least in part, of a material that has elastomeric properties to allow for flexibility of the projections or flaps 314 in an outward direction increase the size of the opening 318 at the tip 308, when required, to allow a menstrual collection device 100 to be expelled through the tip 308. Like the applicator 200, the projections or flaps 314 apply a force on the base 104 of the collection device 100 and the sidewalls thereof which translates to the rim 114, causing the rim 114 to expand from a folded state to a fully open state to create a seal with the vaginal cavity without the need to substantially adjust the collection device 100. Once a force is no longer applied to the projections or flaps 314 to push the menstrual collection device 100 therethrough, the projections or flaps 314 automatically and instantly return to their original resting state or closed position.

Figure 18:
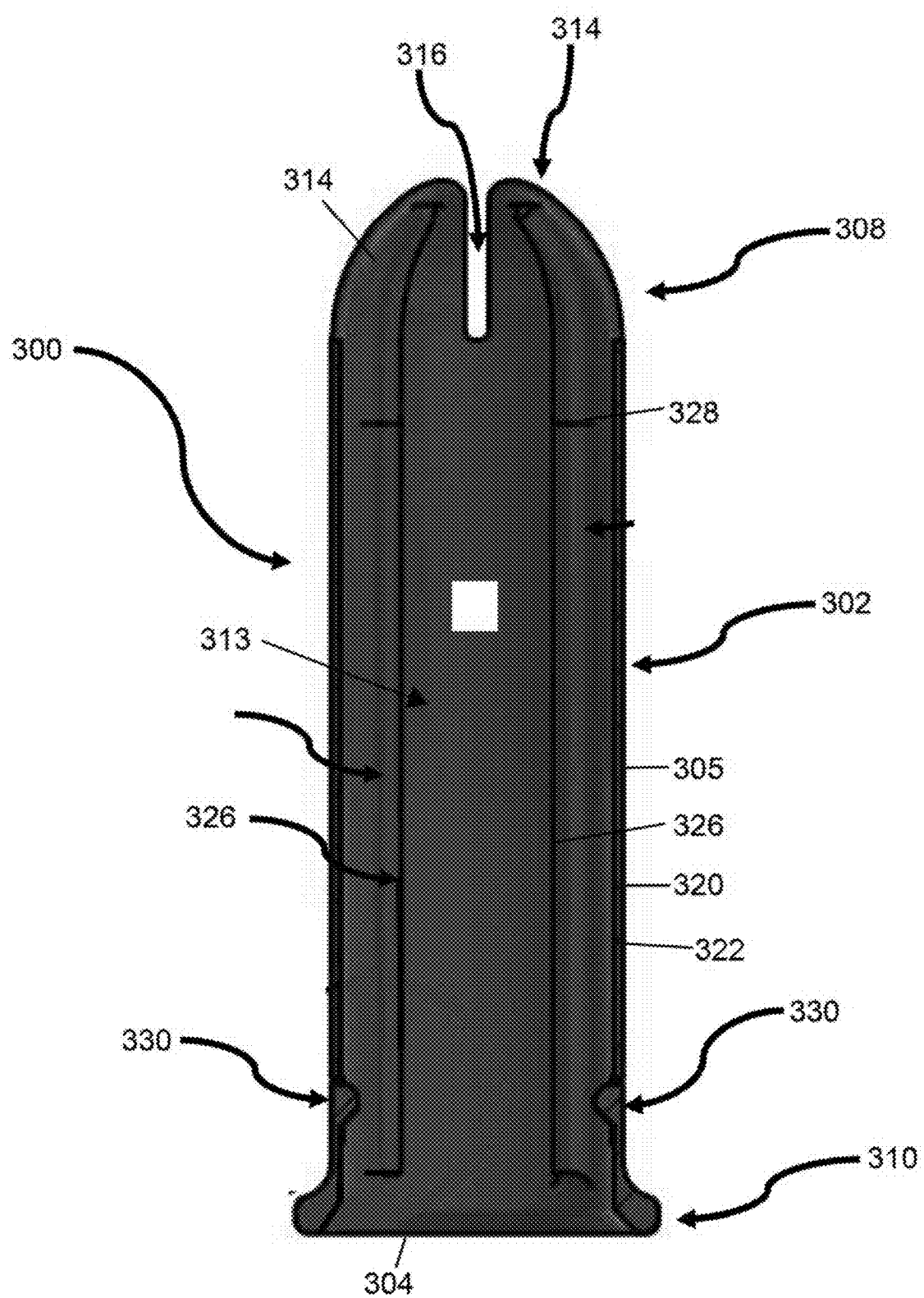
FIG. 18 is a cross-sectional view of the applicator taken along line E-E of FIG. 17.
Figure 19:
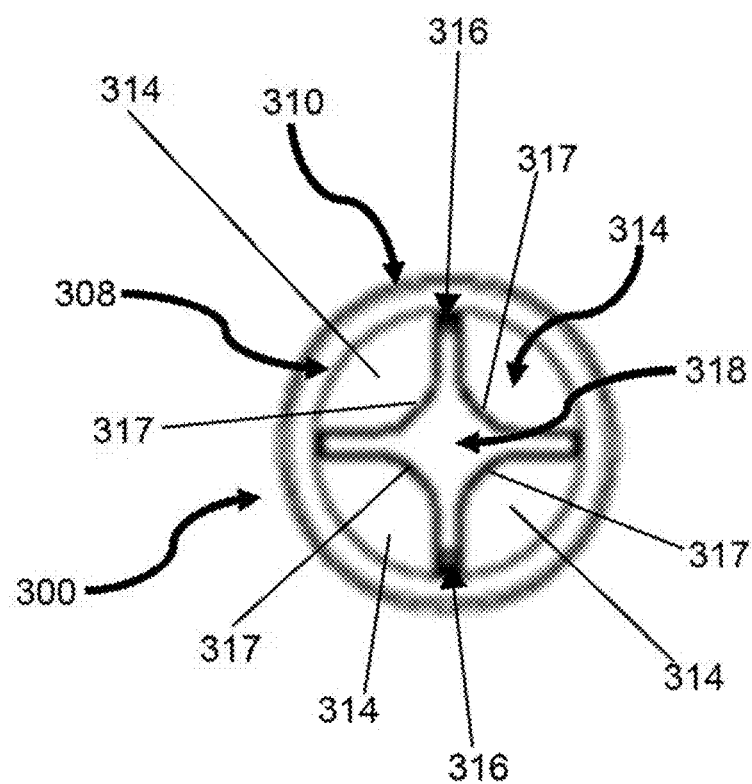
FIG. 19 is a top view of the applicator of FIG. 17.

As illustrated in FIGS. 18-19, the base 310 of the body 302 has a cylindrical shape that flares outwardly such that the outer periphery of the base 310 is wider than the circumference of an external surface 320 of the sidewall 306 of the housing 302.

As can be seen in FIG. 18, the housing 302 of the applicator 300 includes an inner surface 322 that defines the cavity 314 of the housing 302. Guide rails 326 are attached to or formed integral with the inner surface 322 of the housing 302 and extend from the base 310 to an apex of each flap 314 of the housing 302. As can be seen for example in FIGS. 18 and 20, the guide rails 326 are substantially centered on each projection or flap 314. The guide rails 326 are configured to align with and stabilize the plunger 304 when it is used to push the menstrual collection device 100 through the opening 318 at the tip 308 of the housing 302 and reduce the surface area of the menstrual collection device 100 that comes into contact with the inner surface 322 of the applicator housing 302 during insertion of the menstrual collection device 100 within the cavity 324 of the housing 302 and movement of the menstrual collection device 100 through the cavity 324 of the applicator housing 302. The guide rails 326 can include projections 328 that aid in urging the menstrual collection device 100 away from and in contact with the inner surface 322 of the sidewall 306 of the housing 302. The reduced contact of the menstrual collection device 100 with the inner surface 322 of the housing 302 reduces the friction between the collection device 100 and housing 302 and in turn allows the collection device 100 to move easier about the cavity 324 of the housing 302 than would have been the case without the guide rails 326.

To further align and stabilize the plunger 304 within the housing 302, flexible tabs 330 are fixed, at least in part, the outer surface 320 of the sidewall 306 of the housing 302, above the intersection of the sidewall 306 and the base 310. The tabs 330 are configured to interact with the plunger 304 to retain the plunger 304 within the housing cavity 324 when a force is applied to the plunger 324 in a direction toward the tip 308 of the housing 302 to push the menstrual collection device 100 through the opening 318 at the tip 308 of the housing 302 and into the vaginal canal.

Figure 21:
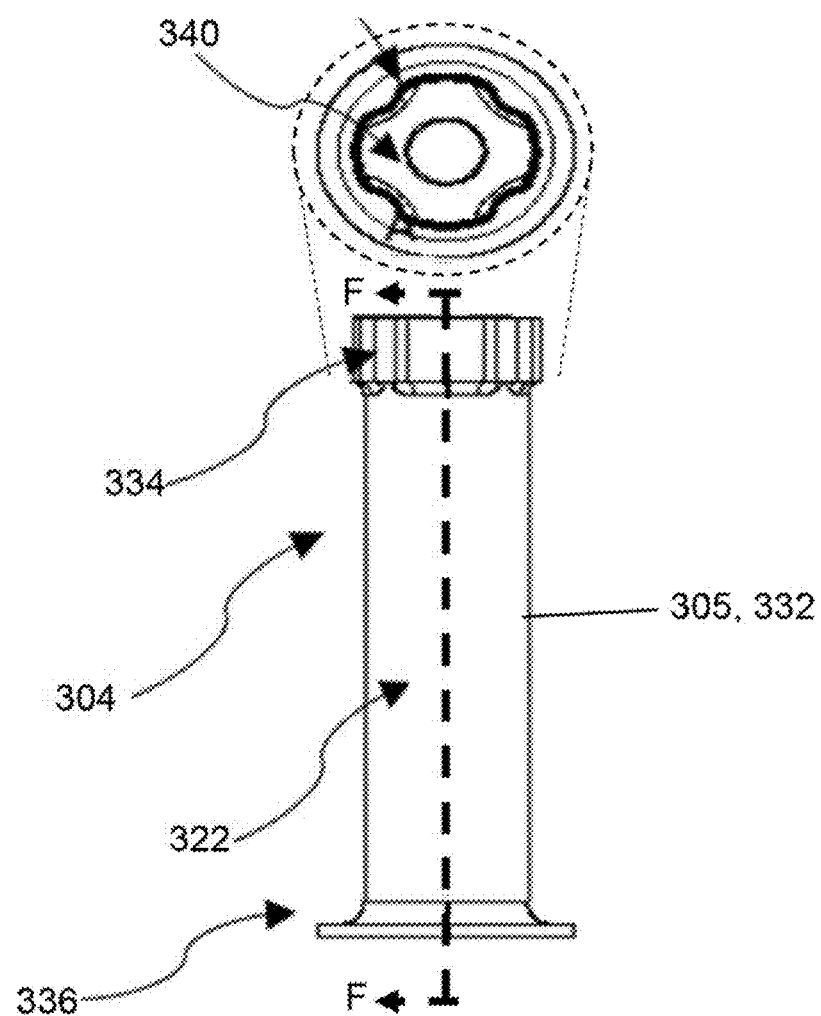
FIG. 21 is a side view of a plunger of the applicator of FIG. 17 with the top view of the plunger in phantom lines that is configured to be arranged within the housing of the applicator of FIG. 17.
Figure 22:
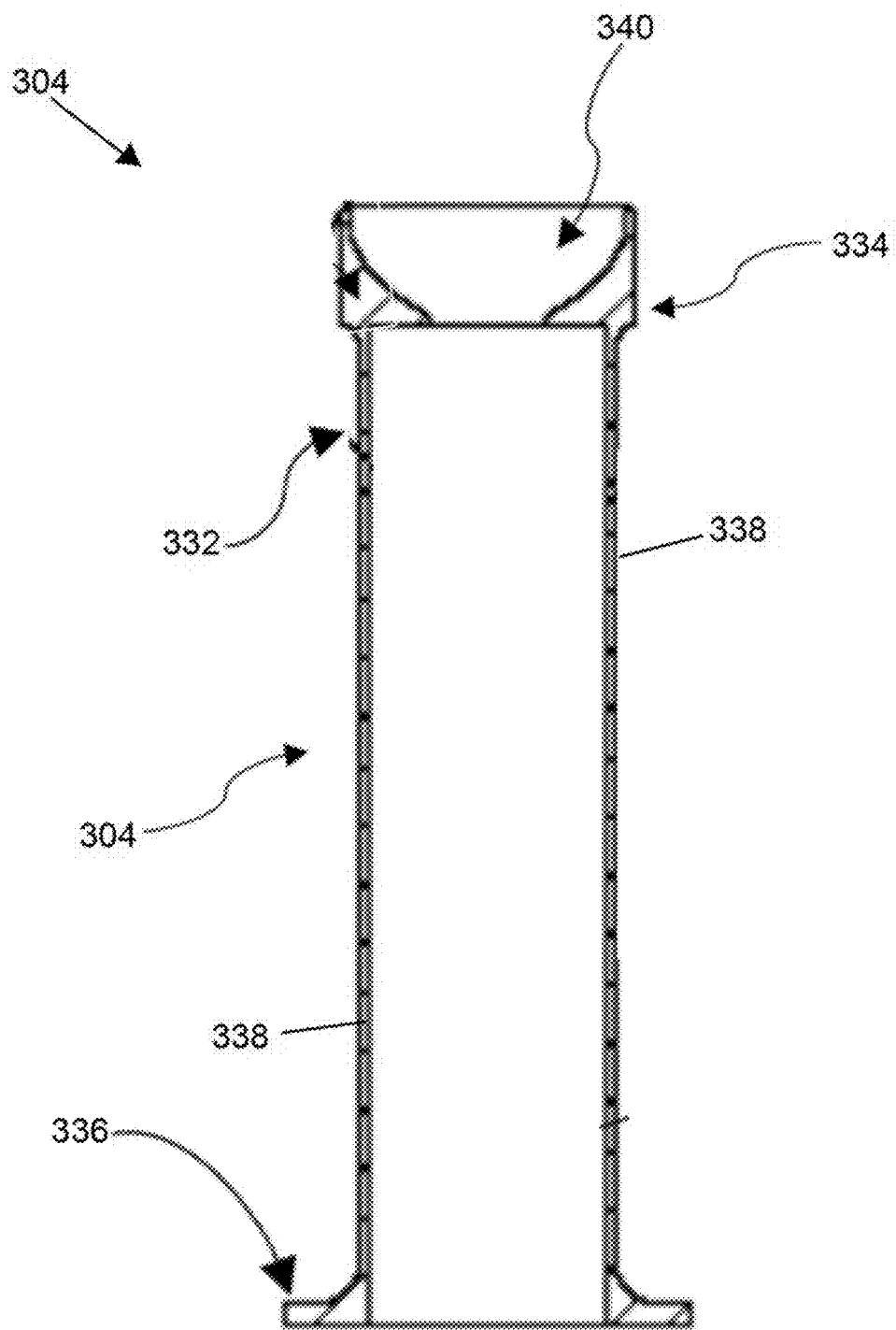
FIG. 22 is a cross-sectional view of the plunger of the applicator of FIG. 17 taken along line F-F of FIG. 21.

FIGS. 21 and 22 illustrate a plunger 304 that includes a body 332 that is delimited at one end by a plunger tip 334 and an opposite end by a plunger base 336. The outer surface of the plunger body 332, which extends linearly between the tip 334 and the base 336, includes a plurality of notches 338 that interact with the projections 328 that extend from the guide rails 326 to further aid in stabilizing and aligning the plunger 304 within the applicator housing 302. A recess 340 extends from the tip 334 of the plunger 304 towards the base 336 thereof. The recess 340, as depicted in FIG. 22, has a collection device-like shape to support at least a portion of a menstrual collection device 100, such as the base 104 and the stem 106 of the menstrual collection device 100 to reduce the likelihood that the menstrual collection device 100 will become pinched or trapped between the inner surface 322 of the sidewall 306 of the applicator 302 and the external surface 305 of the plunger 304 as the menstrual collection device is being pushed within the applicator housing 302 by the plunger 304. Moreover, when the menstrual collection device 100 exits the tip 308 of the housing 302 of the applicator 300, the plunger tip 334 in conjunction with the projections or flaps 314 are configured to aid in the opening of a bowl 102 of a menstrual collection device 100. That is, as the menstrual collection device 100 exits the tip 308 of the applicator housing 302, the projections or flaps 314 apply a force to the first rib 116 and the second rib 118 of the collection device 100 which in turn translates to the housing 102 and rim of the menstrual collection device 100 to facilitate the opening of the housing 102 of the menstrual collection device 100.

Figure 23A:
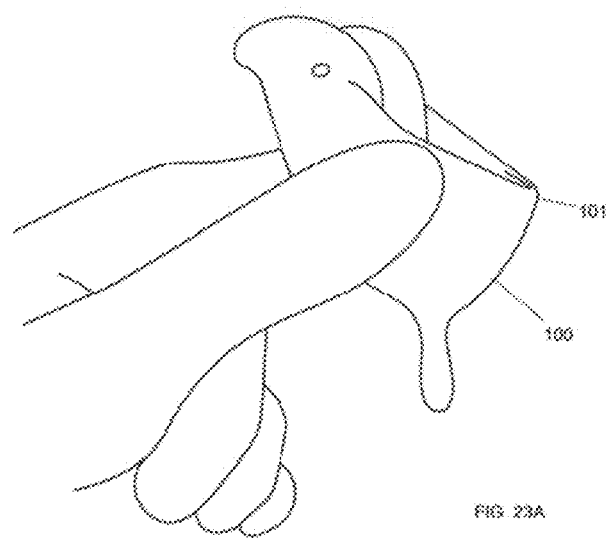
FIGS. 23A-23C are sequentially steps of a method of folding the menstrual collection device of FIG. 1 for insertion into the applicator of FIGS. 9 and 10, FIG. 17 or directly into the vaginal canal.
Figure 23B:
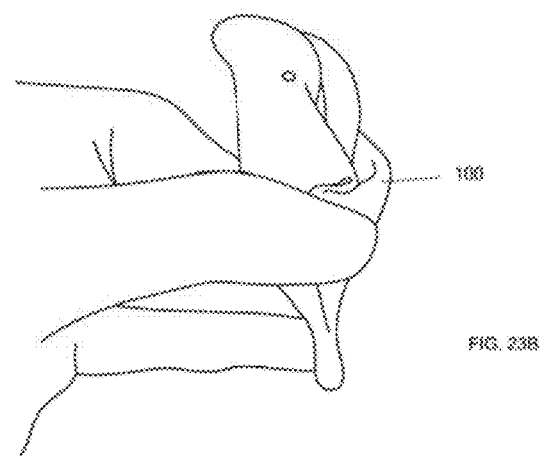
Figure 23C:
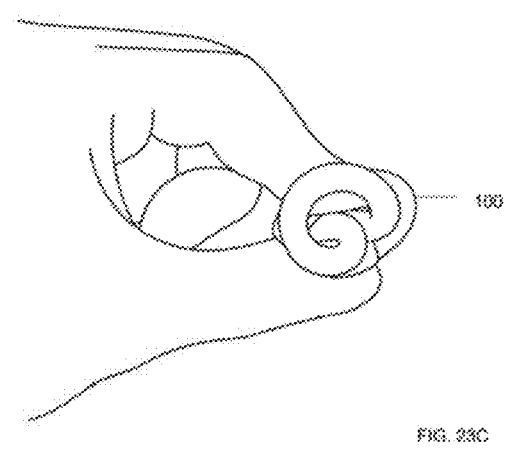

FIGS. 23A-23C depict the menstrual collection device 100 folded in a three-step process for form what is referred to as a punch-down fold. The punch-down fold substantially decreases the diameter of the menstrual collection device 100 to allow the menstrual collection device 100 to either be inserted into the cavity of the applicator 200, 300 or directly into the vaginal canal. The three steps of the punch-down fold method are generally: (1) folding; (2) wrapping; and (3) insertion.

To begin, as can be seen in FIG. 23A, for the folding step a user holds the menstrual collection device 100 in one hand. With the user's free hand, the user places their fingers on the rim 114 of the menstrual collection device 100 in line with the first rib 116 and pushes or punches down on the rim 114 from the outer surface 124 of the collection device 100 towards the second rib 118, collapsing the rim 114 and partially collapsing the sidewall of the collection device 100. When the portion of the rim 114 to which force is being applied contacts the inner surface 128 of the bowl 102, near the base 104 of the bowl 102, the user then pinches the membrane 112 on both sides of the first rib 116 together to hold the fold, which encompasses a portion of the first rib 116 and rim 114 in place within the cavity 109 of the bowl 102. The portion of the first rib 116 and the portion of the membrane 112 that remain untucked form a corner 101.

Next, as depicted in FIG. 15B, the user performs the wrapping step where the user grips the corner 101 and wraps it left or right around the menstrual collection device 100 towards the second rib 118 forming a twist/swaddle. The twist/swaddle is then gripped by the user to secure the wrapped portion of the menstrual collection device 100 in place. To complete the punch-down fold, the user pinches the twisted/wrapped menstrual collection device 100.

Figure 25:
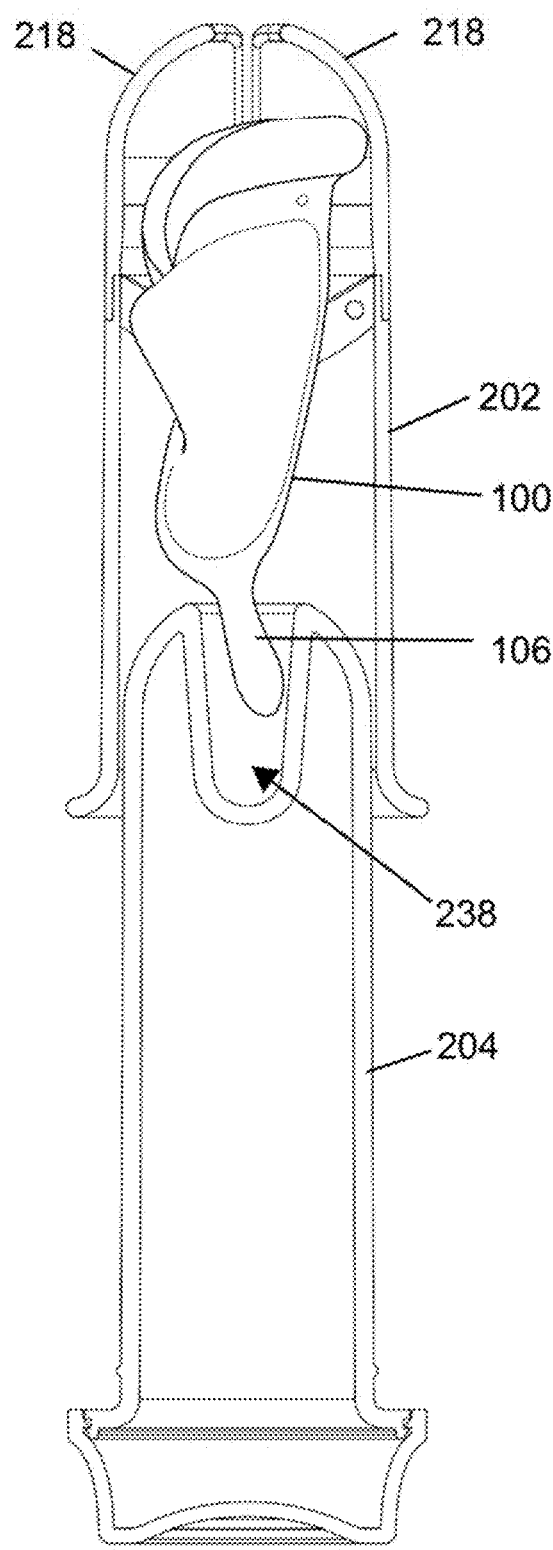
FIG. 25 is a cross-sectional view of the menstrual collection device of FIG. 1 arranged within the applicator body and a portion of the plunger arranged within the body of the applicator of FIGS. 9 and 10.

A top view of the completed punch-down fold is illustrated in FIG. 15C. At this stage, the user can begin to either insert the menstrual collection device 100 into the body 202 of the applicator 200 as shown in FIG. 25 as will be described below or directly into the vaginal canal.

FIGS. 24A-24D depict sequentially a technique commonly referred to as the diamond fold. Generally, the diamond fold is formed in three steps: (1) folding; (2) wrapping; and (3) insertion.

Figure 24A:
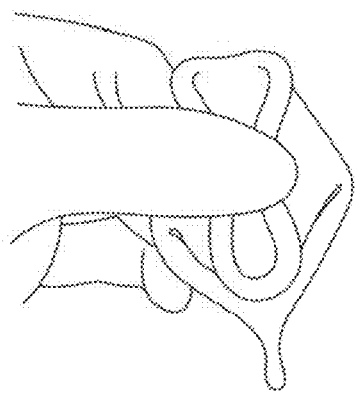
FIGS. 24A-24D are sequentially the steps of another method of folding the menstrual collection device of FIG. 1 for insertion into the applicator of FIGS. 9 and 10, FIG. 16 or directly into the vaginal canal.

For the folding step, a user squeezes the upper rim 114 of the collection device 100 at midpoints between the first rib 116 and the second rib 118 together. The midpoint of the first rib 116 is then pushed inward and the entire top of the menstrual collection device 100, including the pinched rim 114, are folded down over the first rib 116. If done correctly, each side of the membrane 112 of the menstrual collection device 100 should extend outwardly in a diamondlike shape to form a protruding side as shown in FIG. 24A.

Figure 24B:
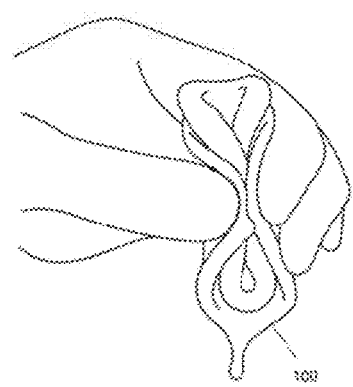
Figure 24C:
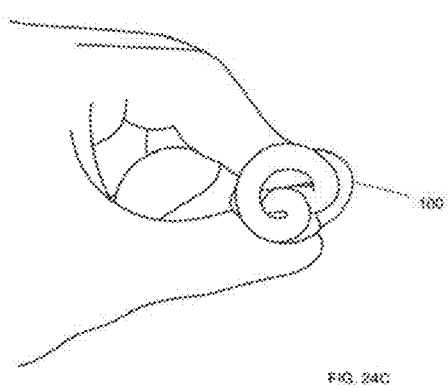
Figure 24D:
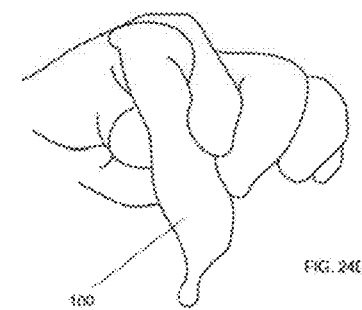

Next, as illustrated in FIG. 24B, the protruding sides of the menstrual collection device 100 are wrapped inward over the top of the pinched rim 114 to complete the diamond fold. FIG. 24C shows an overview of the diamond fold and FIG. 24D shows a sideview of the diamond fold.

After completing the diamond fold, the user can then place the menstrual collection device 100 within the cavity of the applicator body 202, 302 or directly into the vaginal canal. To facilitate the insertion either into the applicator body 202, 302 or vaginal canal, the user can ensure the diamond fold is firmly pinched. The steps and process of inserting the folded collection device 100 into the applicator body 202, 302 are substantially the same as those discussed above for the punch-down fold.

To insert the menstrual collection device 100 into the applicator body 202, as shown in FIG. 25, the user orients the top of the collection device 100 into the open end 108 of the applicator body 202 and pushes the menstrual collection device 100 into the cavity 216 of the applicator body 202 until it reaches the distal end of the cavity 216 of the applicator body 202. If the collection device 100 cannot be pushed all the way into the applicator body 202 manually, the plunger 204 can be inserted into the applicator cavity 216 and push the collection device 100 toward the distal end of the body 202 to prepare the transfer of the menstrual collection device 100 from the applicator 200 into the vaginal canal.

The plunger 204 further aids to orients the collection device 100 within the applicator 100 and reduce or minimize friction between the collection device 100 and inner wall 214 of the housing 202 to reduce the surface area of the collection device 100 in contact with the inner wall 214 by nesting or arranging within the cavity 238 of the plunger the stem 106 and at least part of the base 104. It is noted that while the applicator 200 is depicted in conjunction with the collection device 100 that the applicator 300 could alternatively be used.

Figure 26:
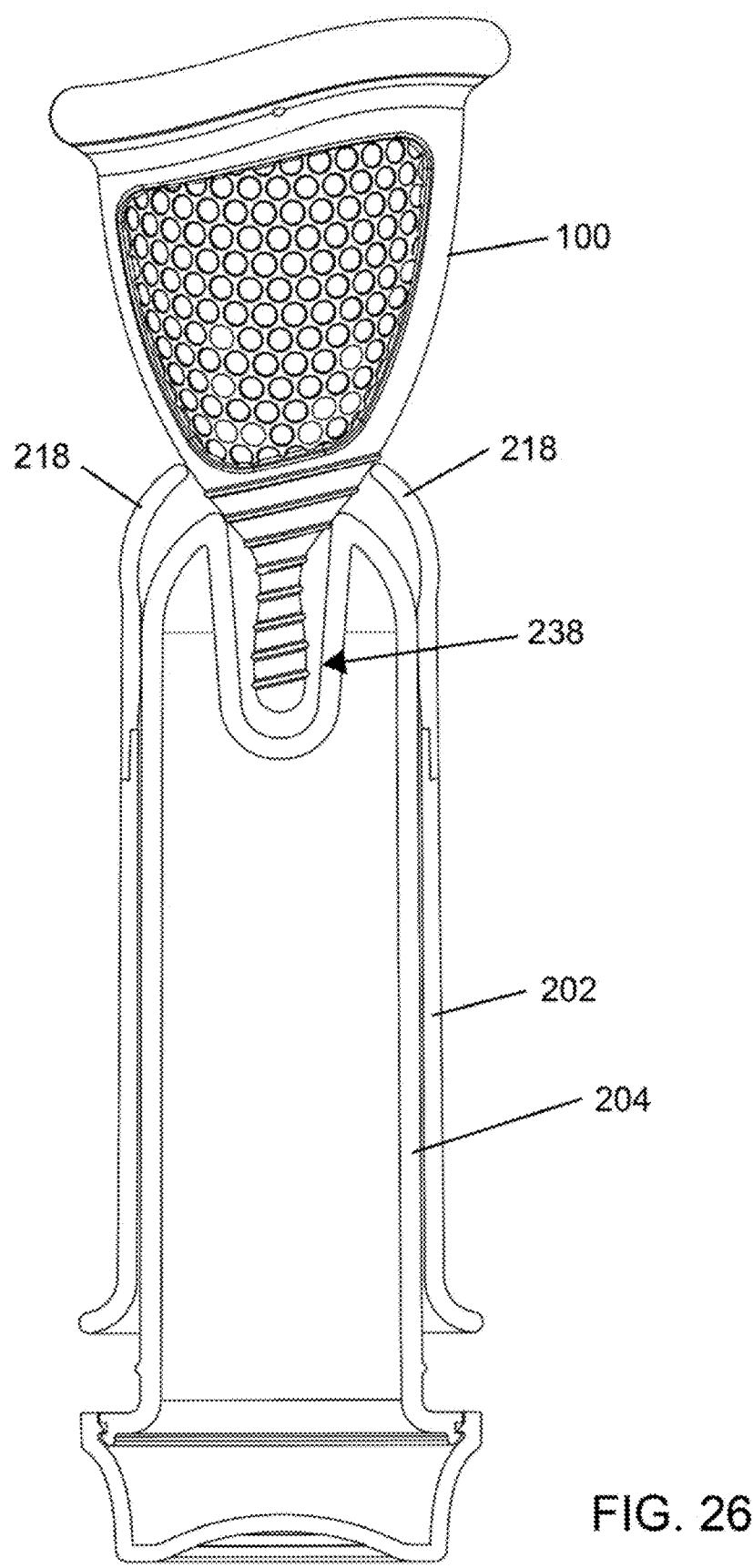
FIG. 26 is a cross-sectional view of the menstrual collection device of FIG. 1 being forced out of the applicator body by the plunger of the applicator of FIGS. 9 and 10.
Figure 27:
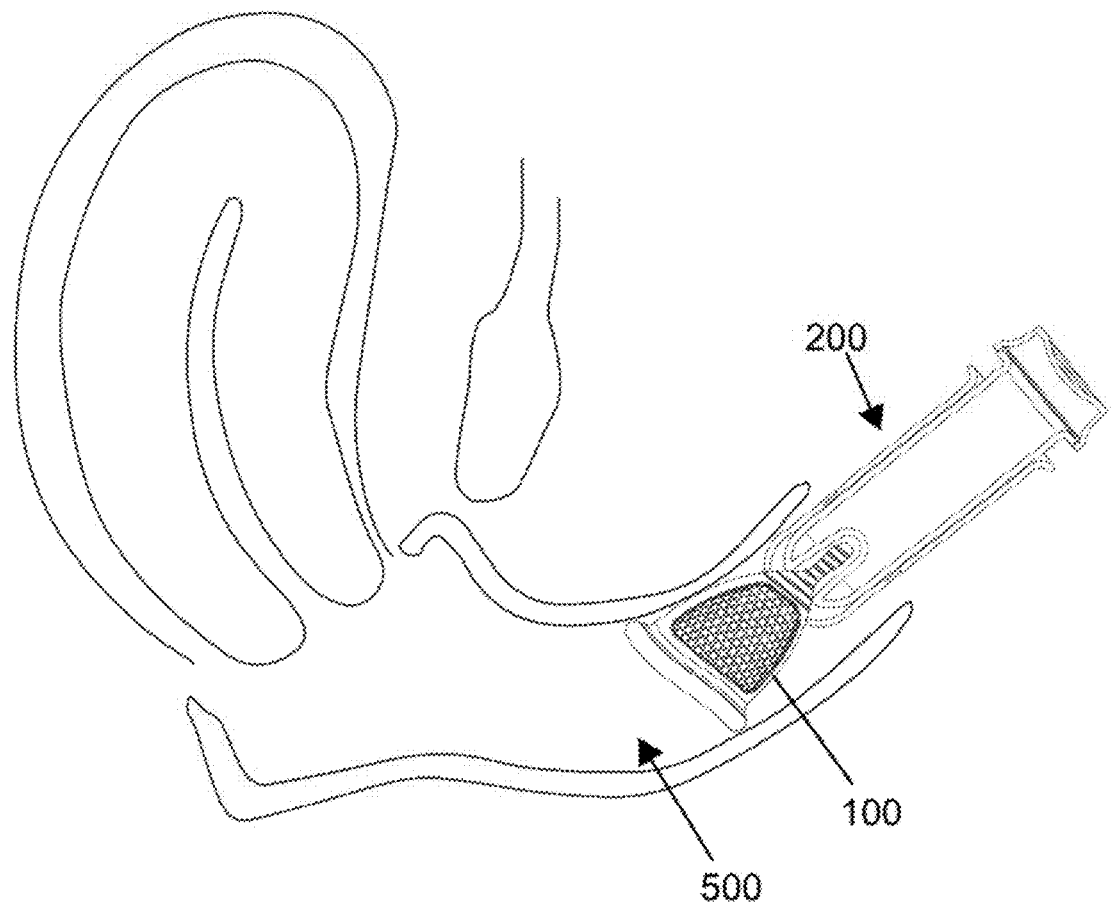
FIG. 27 is a view depicting the insertion of the menstrual collection device into the vaginal canal utilizing the applicator of FIGS. 9 and 10.

As shown in FIGS. 26 and 27, to move the menstrual collection device 100 through the opening 222 at the tip 208 of the applicator body 202, a force is applied to the base 230 of the plunger 204, moving the plunger 204 and in turn menstrual collection device 100 toward the tip 208 of the applicator body 202. As the menstrual collection device 100 exits the tip 208 of the housing 202 of the applicator 200, the plunger 204 in conjunction with the flaps 218 are configured to aid in the opening of the of menstrual collection device 100. That is, once the rim 114 of the menstrual collection device 100 extends through the distal end of the tip 208 of the applicator 200, the projections or flaps 218 of the tip 208 begin to retract to apply a compressive force to the base 104, sidewall 128 and/or ribs 116, 118, 102, 122 of the collection device 100, which translates to the rim 114 to force the rim 114 to expand the device 100 to a fully open state. This compressive force interaction between the projections or flaps 218 and the base 104 of the collection device 100 significantly reduce the need for users to manually adjust the collection device 100 to achieve a fully-opened collection device state. The specific geometry and material properties of the tip 208 of the applicator 200 create a member that applies a compressive force which ensures that the device 100 regularly fully opens, while still allowing for the projections or flaps 218 to flex back outwards when the applicator 200 is retracted out of the vaginal canal to prevent the device 200 from adjusting the position of the collection device 100 during the retracting process.

Figure 28:
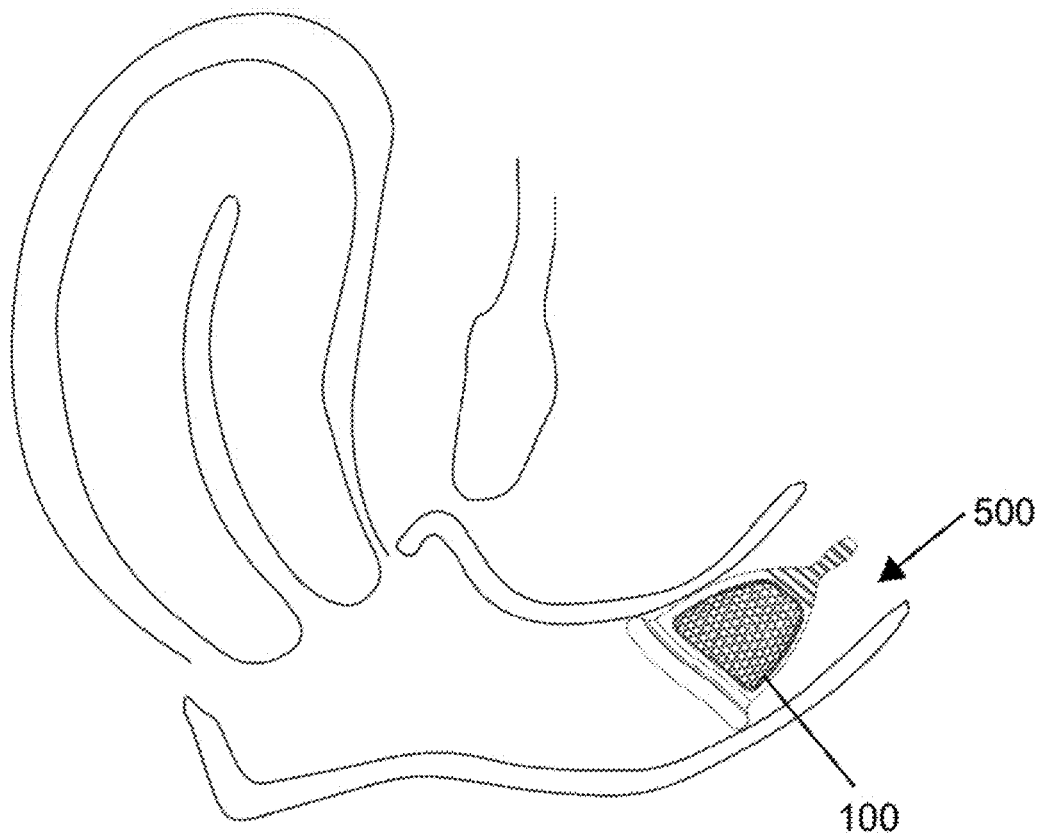
FIG. 28 is a view showing the menstrual collection device of FIG. 1 in a fully deployed or open state within the vaginal canal.

FIG. 28 depicts the menstrual collection device 100 fully deployed within the vaginal cavity 500.

Although the description above and accompanying drawings contains much specificity, the details provided should not be construed as limiting the scope of the embodiments, but merely as describing some of the features of the embodiments. The description and figures should not to be taken as restrictive and are understood as broad and general teachings in accordance with the present invention. While the embodiments have been described using specific terms, such description is for illustrative purposes only, and it is to be understood that modifications and variations to such embodiments, including, but not limited to, the substitutions of equivalent features and terminology may be readily apparent to those of skill in the art based upon this disclosure without departing from the spirit and scope of the invention.

What is claimed is:

1. A method of inserting a reusable menstrual collection device into a vaginal canal, the method comprising:
   a) providing a reusable menstrual collection device capable of collecting period fluid, comprising a circumference, a housing that is open at a first end and tapers to a base at a second end from which a stem extends, wherein the housing defines a cavity therein, and wherein the housing comprises includes a frame having a first thickness, wherein the frame comprises two vertical ribs, and wherein the housing further comprises two panels having a second thickness and extending between the frame two vertical ribs, and wherein the housing further comprises a rim extending from the frame to delimit the housing first end;

b) providing a reusable applicator of capable of inserting the menstrual collection device, comprising a housing and a plunger, wherein:

i) the applicator housing comprises a circumference, a sidewall that is delimited at a first end by a tip and a second end by a base, and a first, outer surface, and a second, inner surface, wherein the second surface defining defines a cavity that extends within the housing from the base to the tip;

ii) the applicator plunger is fully separable from the applicator housing and is arrangeable within the cavity of the applicator housing, and wherein the plunger comprises a cylindrical main body that extends between a first end and a second end, the first end including a stem cavity and the second end defined by a plunger base, wherein the stem cavity extends toward the second end, and wherein the plunger base comprises an outer periphery that is greater than an outer periphery of the main body;

iii) the circumference of the menstrual collection device is greater than the circumference of the applicator housing;

c) folding the menstrual collection device to reduce its circumference;

d) loading the first end of the folded menstrual collection device into the applicator housing cavity;

e) arranging the loaded menstrual collection device within the applicator housing cavity such that the stem is in a position to engage with the plunger stem cavity;

f) engaging the plunger stem cavity with the stem and inserting the first end of the plunger into the applicator housing cavity;

g) inserting at least the tip of the applicator housing into a vaginal canal;

h) moving the first end of the plunger towards the tip of the applicator housing such that the menstrual collection device contacts the applicator housing projections;

i) pushing the plunger towards the tip of the applicator housing with a force that causes the housing projections to expand an opening at the tip of the housing of the applicator and allow the folded menstrual collection device to pass through the opening and expand to an unfolded state within the vaginal canal; and j) retracting the applicator from the vaginal canal.

2. The method of claim 1, wherein the tip of the applicator includes a plurality of projections that extend in a curved manner from the sidewall toward an apex of the tip and are spaced from each other by gaps that extend into an opening, and wherein the projections comprise rounded edges.

3. The method of claim 1, wherein the first thickness of the frame is greater than the second thickness of the panels.

4. The method of claim 2, wherein the projections apply a force on the collection device which translates to the rim thereof, causing the rim to expand from a folded state to a fully open state to create a seal with the vaginal cavity canal.

5. The method of claim 4, wherein the projections return to an original resting state when no force is applied thereto.

* * * * *